US012773131B1

(12) United States Patent
French

(10) Patent No.: US 12,773,131 B1
(45) Date of Patent: Oct. 27, 2026

(54) METHOD OF EVALUATION OF INVOLVING PHYSICAL TASKS AND NEUROLOGICAL INPUT

(71) Applicant: Barry James French, Bay Village, OH (US)

(72) Inventor: Barry James French, Bay Village, OH (US)

( * ) Notice: Subject to any disclaimer, the term of this patent is extended or adjusted under 35 U.S.C. 154(b) by 253 days.

(21) Appl. No.: 15/600,982

(22) Filed: May 22, 2017

Related U.S. Application Data

(63) Continuation-in-part of application No. 15/075,628, filed on Mar. 21, 2016, now abandoned.
(Continued)

(51) Int. Cl.
*A61B 5/11* (2006.01)
*A61B 5/00* (2006.01)
*A61B 5/024* (2006.01)
*A61B 5/16* (2006.01)
*A63B 69/00* (2006.01)
(Continued)

(52) U.S. Cl.
CPC ............ *A61B 5/1124* (2013.01); *A61B 5/024* (2013.01); *A61B 5/162* (2013.01); *A61B 5/744* (2013.01); *A61B 5/1118* (2013.01); *A61B 5/112* (2013.01); *A61B 2503/10* (2013.01); *A61B 2505/09* (2013.01); *A61B 2562/0219* (2013.01); *A63B 69/0022* (2013.01); *A63F 13/814* (2014.09); *A63F 2300/8047* (2013.01);
(Continued)

(58) Field of Classification Search
CPC ........... A63F 13/814; A63F 2300/8047; A61B 2562/0219; A61B 2503/10; A61B 5/1118; A61B 2505/09; A61B 5/112; A61B 5/1124; A61B 5/024; A61B 5/162; A61B 5/744; A63B 69/0022; A63B 13/814; A63B 2300/8047; G09B 19/003; G09B 19/0038; G09B 19/0015
See application file for complete search history.

(56) References Cited

U.S. PATENT DOCUMENTS 4,761,005 A 8/1988 French et al.
4,824,107 A 4/1989 French
(Continued)

FOREIGN PATENT DOCUMENTS

EP 0590101 B1 4/1994
WO 2004008427 A1 1/2004

OTHER PUBLICATIONS

Leddy, John J., et al., "Reliability of a Graded Exercise Test for Assessing Recovery From Concussion", Clinical Journal of Sports Medicine, (Mar. 2011), vol. 21, No. 2, pp. 89-94.
(Continued)

*Primary Examiner* — Jack Yip
(74) *Attorney, Agent, or Firm* — McDonald Hopkins LLC

(57) ABSTRACT

Multi-task (MT) paradigms may be used to evaluate a subject in a recreation of cognitive and motor/movement challenges inherent in dynamic environments, such as those encountered during sports. Such paradigms provide multiple tasks that the subject must engage in at the same time. MT paradigms include dual-task (DT) paradigms, in which the subject engages in a task that requires the subject to perform two tasks simultaneously, and triple-task (TT) paradigms, in which the subject engages in a task that requires the subject to perform two tasks simultaneously.

17 Claims, 20 Drawing Sheets

Related U.S. Application Data

(60) Provisional application No. 62/414,761, filed on Oct. 30, 2016, provisional application No. 62/284,932, filed on Oct. 14, 2015.

(51) Int. Cl.
*A63F 13/814* (2014.01)
*G09B 19/00* (2006.01)

(52) U.S. Cl.
CPC ........ *G09B 19/0015* (2013.01); *G09B 19/003* (2013.01); *G09B 19/0038* (2013.01)

(56) References Cited

U.S. PATENT DOCUMENTS

| | | | |
|---|---|---|---|
| 4,883,271 | A | 11/1989 | French |
| 5,099,702 | A | 3/1992 | French |
| 5,249,967 | A | 10/1993 | O'Leary et al. |
| 5,469,740 | A | 11/1995 | French et al. |
| 5,524,637 | A | 6/1996 | Erickson |
| 6,073,489 | A | 6/2000 | French et al. |
| 6,098,458 | A | 8/2000 | French et al. |
| 6,308,565 | B1 | 10/2001 | French et al. |
| 6,430,997 | B1 | 8/2002 | French et al. |
| 6,734,834 | B1 | 5/2004 | Baram |
| 6,749,432 | B2 | 6/2004 | French et al. |
| 6,765,726 | B2 | 7/2004 | French et al. |
| 6,876,496 | B2 | 4/2005 | French et al. |
| 7,038,855 | B2 | 5/2006 | French et al. |
| 7,359,121 | B2 | 4/2008 | French et al. |
| 7,602,301 | B1 | 10/2009 | Stirling et al. |
| 7,634,379 | B2 | 12/2009 | Noble |
| 7,771,320 | B2 | 8/2010 | Riley et al. |
| 7,791,808 | B2 | 9/2010 | French et al. |
| 7,864,168 | B2 | 1/2011 | French |
| 8,048,002 | B2 | 11/2011 | Ghajar |
| 8,165,844 | B2 | 4/2012 | Luinge et al. |
| 8,342,978 | B2 | 1/2013 | Tamura |
| 8,503,086 | B2 | 8/2013 | French et al. |
| 8,529,448 | B2 | 9/2013 | McNair |
| 8,568,311 | B2 | 10/2013 | LaPlaca et al. |
| 8,671,784 | B2 | 3/2014 | Nishibayashi |
| 8,679,037 | B2 | 3/2014 | Sarig-Bahat |
| 10,258,259 | B1 * | 4/2019 | Zets ..................... A61B 5/7455 |
| 2001/0015123 | A1 | 8/2001 | Nishitani et al. |
| 2005/0153265 | A1 * | 7/2005 | Kavana .................. G10H 1/368 434/250 |
| 2006/0035774 | A1 * | 2/2006 | Marks ................ A63B 71/0686 482/148 |
| 2006/0073449 | A1 | 4/2006 | Kumar et al. |
| 2006/0266200 | A1 * | 11/2006 | Goodwin ................ A63F 13/02 84/611 |
| 2008/0090703 | A1 | 4/2008 | Rosenberg |
| 2009/0048044 | A1 | 2/2009 | Oleson et al. |
| 2009/0209308 | A1 * | 8/2009 | Ciarrocchi .............. A63F 13/08 463/1 |
| 2009/0262088 | A1 | 10/2009 | Moll-Carrillo et al. |
| 2009/0270743 | A1 | 10/2009 | Dugan et al. |
| 2010/0103196 | A1 | 4/2010 | Kumar et al. |
| 2011/0270135 | A1 | 11/2011 | Dooley et al. |
| 2012/0143358 | A1 * | 6/2012 | Adams .................... G06F 3/011 700/92 |
| 2012/0183940 | A1 | 7/2012 | Aragones et al. |
| 2013/0132837 | A1 * | 5/2013 | Mead ..................... G06Q 10/10 715/716 |
| 2013/0171596 | A1 | 7/2013 | French |
| 2014/0134584 | A1 | 5/2014 | French |
| 2014/0142439 | A1 | 5/2014 | French |
| 2015/0199917 | A1 | 7/2015 | French |
| 2016/0038788 | A1 * | 2/2016 | McMillan ................. G01L 5/18 73/488 |
| 2017/0157510 | A1 * | 6/2017 | Lowe ...................... A63F 13/30 |
| 2017/0270818 | A1 | 9/2017 | French |

OTHER PUBLICATIONS

Johnson, Philip et al., "Effect of Mild Brain Injury on an Instrumented Agility Task", Clinical Journal of Sports Medicine, (2002), vol. 12, No. 1, pp. 12-17.

"Concussion Management Program", Biodex Medical Systems, Inc., <www.biodex.com/concussion>.

* cited by examiner

Balance Card

| | Baseline | | Current | | Compare | |
|---|---|---|---|---|---|---|
| Date | 01/19/17 09:40 PM | | 02/13/17 02:42 PM | | | |
| | Distance | Misses | Distance | Misses | Distance | Misses |
| Bilateral_Firm | 0.10 | 0 | 0.10 | 0 | 0.00 (0.00 %) | 0.00 (0.00 %) |
| Unilateral_Firm | 0.10 | 4 | 0.10 | 0 | 0.00 (0.00 %) | -4.00 (-100.00 %) |
| Tandem_Firm | 0.10 | 0 | 0.10 | 0 | 0.00 (0.00 %) | 0.00 (0.00 %) |
| Bilateral_Soft | 0.10 | 0 | 0.10 | 0 | 0.00 (0.00 %) | 0.00 (0.00 %) |
| Unilateral_Soft | 0.10 | 0 | 0.10 | 0 | 0.00 (0.00 %) | 0.00 (0.00 %) |
| Tandem_Soft | 0.10 | 0 | 0.10 | 0 | 0.00 (0.00 %) | 0.00 (0.00 %) |

Score Card

| | Baseline | Current | Compare |
|---|---|---|---|
| Date | 01/19/17 04:45 PM | 02/13/17 09:46 AM | |
| Points | 90 | 85 | -5.00 (-5.56 %) |
| Max Level | 5 | 3 | -2.00 (-40.00 %) |
| Total Distance | 640.10 ft (0.121 mi) | 488.70 ft (0.093 mi) | -151.40 (-23.65 %) |
| Total Time | 05:22 | 04:02 | -01:-20.00 (-24.84 %) |
| Calories | 142.86 | 25.24 | -117.61 (-82.33 %) |
| Avg. Heart Rate | 104.28 BPM | 117.21 BPM | 12.93 (12.40 %) |
| Max Heart Rate | 112.00 BPM | 173.00 BPM | 61.00 (54.46 %) |
| Avg. Speed | 3.95 ft/sec (2.695 mph) | 3.86 ft/sec (2.631 mph) | -0.09 (-2.38 %) |
| Max Speed | 6.64 ft/sec (4.528 mph) | 6.82 ft/sec (4.652 mph) | 0.18 (2.72 %) |
| Avg Jump Height | 3.57 in | 4.57 in | 1.00 (28.03 %) |
| Max Jump Height | 11.66 in | 15.12 in | 3.45 (29.62 %) |

FIG. 13

Reaction Time
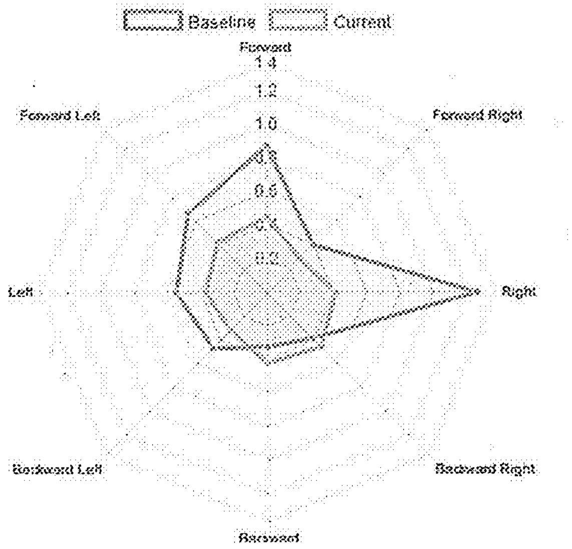
| | Baseline | Current | Compare |
|---|---|---|---|
| Forward | 0.87 | 0.45 | -0.42 (-48.54 %) |
| ForwardRight | 0.40 | 0.28 | -0.12 (-30.82 %) |
| Right | 1.26 | 0.42 | -0.85 (-67.14 %) |
| BackwardRight | 0.39 | 0.46 | 0.07 (18.11 %) |
| Backward | 0.32 | 0.42 | 0.10 (29.91 %) |
| BackwardLeft | 0.47 | 0.32 | -0.15 (-32.57 %) |
| Left | 0.55 | 0.37 | -0.17 (-31.79 %) |
| ForwardLeft | 0.67 | 0.42 | -0.24 (-36.58 %) |
| L/R Difference | 57% R | 10% R | |
Speed
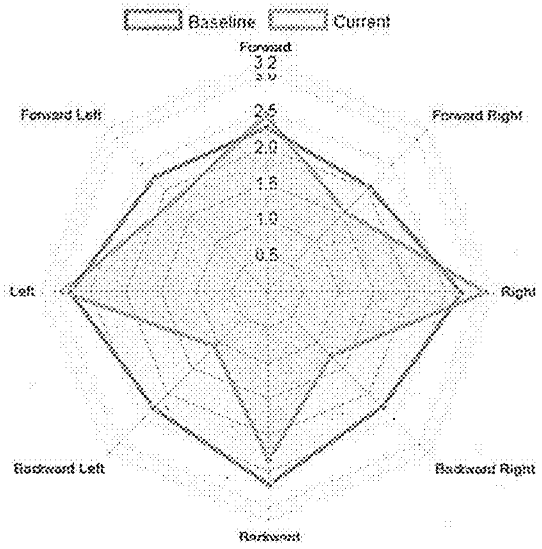
| | Baseline | Current | Compare |
|---|---|---|---|
| Forward | 2.28 | 2.46 | 0.18 (7.80 %) |
| ForwardRight | 2.06 | 1.55 | -0.50 (-24.52 %) |
| Right | 2.74 | 3.08 | 0.34 (12.39 %) |
| BackwardRight | 2.28 | 1.26 | -1.03 (-44.91 %) |
| Backward | 2.70 | 2.34 | -0.36 (-13.16 %) |
| BackwardLeft | 2.29 | 1.06 | -1.23 (-53.87 %) |
| Left | 2.79 | 2.91 | 0.12 (4.25 %) |
| ForwardLeft | 2.25 | 1.80 | -0.45 (-19.95 %) |
| L/R Difference | 2% L | 6% R | |
G. 14 A

Acceleration
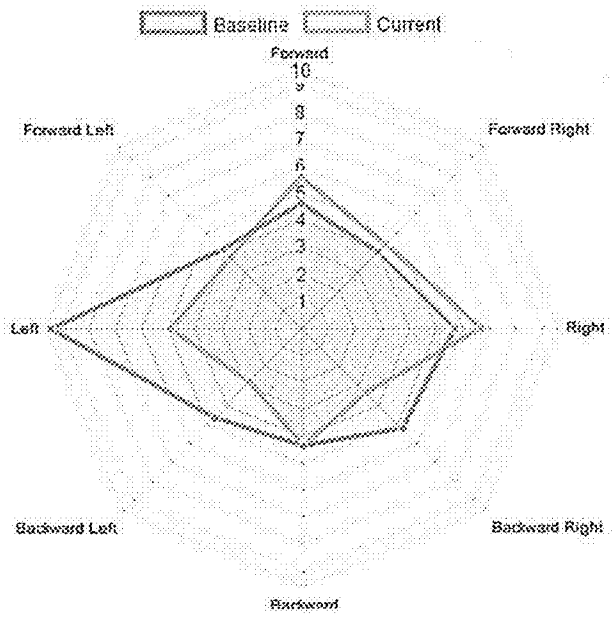
| | Baseline | Current | Compare |
|---|---|---|---|
| Forward | 4.64 | 5.66 | 1.02 (22.09 %) |
| ForwardRight | 3.99 | 4.43 | 0.44 (10.99 %) |
| Right | 5.68 | 6.70 | 1.02 (17.97 %) |
| BackwardRight | 5.25 | 3.40 | -1.85 (-35.23 %) |
| Backward | 4.39 | 4.38 | -0.01 (-0.30 %) |
| BackwardLeft | 4.71 | 2.79 | -1.92 (-40.70 %) |
| Left | 9.45 | 4.93 | -4.51 (-47.79 %) |
| ForwardLeft | 4.16 | 3.81 | -0.35 (-8.46 %) |
| L/R Difference | 40% L | 26% R | |
Deceleration
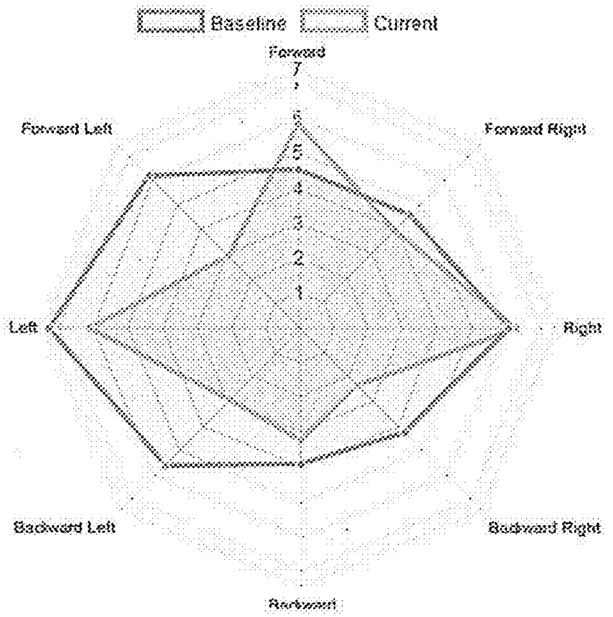
| | Baseline | Current | Compare |
|---|---|---|---|
| Forward | -4.57 | -5.86 | -1.29 (28.17 % |
| ForwardRight | -4.60 | -3.97 | 0.62 (-13.59 % |
| Right | -6.12 | -6.32 | -0.20 (3.34 %) |
| BackwardRight | -4.29 | -2.34 | 1.95 (-45.46 % |
| Backward | -3.94 | -3.24 | 0.70 (-17.85 %) |
| BackwardLeft | -5.66 | -2.93 | 2.73 (-48.20 %) |
| Left | -7.32 | -6.13 | 1.18 (-16.18 %) |
| ForwardLeft | -6.21 | -2.92 | 3.29 (-52.93 %) |
| L/R Difference | 16% L | 3% R | |
FIG. 14 B

| | *EXCELLENT* | *GOOD* | *AVERAGE* |
|---|---|---|---|
| *REACTION TIME*<br>*The elapsed time from presentation*<br>*Of a cue to initial correct response* | *</= .65 secs* | *.66-.85 secs* | *>/= .86 secs* |
| *SPEED in feet per second*<br>*How fast? The distance traveled*<br>*Per unit of time* | *>/= 5.3 ft/sec* | *3.6-4.2 ft/sec* | *</- 3.5 ft/sec* |
| *ACCELERATION/1$^{st}$ STEP QUICKNESS*<br>*The rate at which the subject*<br>*Changes speed* | *>/= 27.2 ft/sec$^2$* | *13.7-27.7 ft/sec$^2$* | *<13 ft/sec$^2$* |
| *DECELERATION/BRAKING*<br>*The rate at which the subject changes*<br>*Speed; Expressed as a negative number* | *>/= -19.4 ft/sec$^2$* | *-19.03 to -9.18 ft/sec$^2$* | *</= -9.17 ft/sec$^2$* |

FIG. 15

METHOD OF EVALUATION OF INVOLVING PHYSICAL TASKS AND NEUROLOGICAL INPUT

RELATED APPLICATIONS

This application is a continuation-in-part of U.S. application Ser. No. 15/075,628, filed Mar. 21, 2016, which claims priority under 35 USC 119 to U.S. Provisional Application 62/284,932, filed Oct. 14, 2015. This application also claims priority under 35 USC 119 to U.S. Provisional Application 62/414,761, filed Oct. 30, 2016. All of the foregoing applications are incorporated by reference herein in their entireties.

FIELD OF THE INVENTION

The invention is in the field of methods of evaluating subjects for physical and/or neurological performance.

DESCRIPTION OF THE RELATED ART

Sports-related concussions are often diagnosed using a battery of single-task tests, including clinical evaluations, cognitive functioning, postural control, and self-reported symptoms. Current methods practiced may involve the measurement of isolated capabilities such as leg strength, range of motion, as well as speed and agility drills that are preplanned, i.e. known in advance to the subject. None of these adequately challenge the subject's sensory, cognitive and neuromuscular systems. While single-task paradigms effectively measure either cognitive functioning or postural control, these paradigms may be limited as they only evaluate domains in isolation and not the interaction of these domains across concurrent tasks.

In the field of experimental psychology, a dual-task (DT) paradigm is defined as a task that requires the subject to perform two tasks simultaneously, so that this effort can be compared to his/her performance under single-task conditions. DT paradigms are frequently employed in both research and healthcare environments to assess the cognitive and motor performance/status of an individual who may, by way of example, has suffered a concussion (brain injury) or other neuromuscular "insult", orthopedic injury or similar. A real world example of a DT paradigm is driving a car; the driver must concentrate on navigating her car down the road while simultaneously maintaining the prescribed speed limit.

Present DT approaches include, by way of example, the subject walking up stairs while tasked with counting down by 3s out loud. While this DT approach provides two distinct tasks, i.e., the walking up stairs and the "distraction" of counting down out loud, it fails to accurately replicate the cognitive, motor and cardiorespiratory challenges inherent in reaction-based sports as well as other physically demanding weight-bearing activities.

Accordingly there is a need for improvements in diagnosing and evaluating concussions and other cognitive/neurological/physical capabilities

SUMMARY OF THE INVENTION

The following features, described in terms of aspects and embodiments of the invention, may be combined in any combination into a single method/system.

Aspects of the present invention involve sports simulation to replicate the dynamic environment of reaction-based sports using multi-task (MT) paradigms, such as dual task (DT) paradigms or triple task (TT) paradigms. This provides a more sensitive, objective and accurate MT paradigm of actual sports. This enhanced sensitivity aids in the detection of signs of overtraining syndrome as well as heightened risk of orthopedic and brain injuries.

Aspects of the present invention provide enhanced sensitivity and novel analytics for detecting signs of overtraining syndrome and increased risk of orthopedic and brain injuries.

According to an aspect of the invention, a sport simulation incorporates a DT ("divided attention") paradigm that more profoundly challenges the athlete's sensory, cognitive and motor prowess resulting in enhanced measurement sensitivity and relevance for exercise prescription management and injury prevention.

According to an aspect of the invention, a method of evaluation uses a TT paradigm to detect previously-undetectable movement asymmetries and performance deficits for applications that range from return to physical activities post a lower extremity orthopedic (such as a knee or ankle) injury, a neurological injury (such as a concussion), or for assessing the risk for falling/mobility in aging populations, to give a few examples.

According to an aspect of the invention, an MT paradigm method of evaluation involves use of a screen/interface that displays a virtual environment that may have both an analog and digital "speedometer," providing an indication of the desired work load (rate of movement) of the subject, and the actual work load (rate of movement). Both these meters serve to update the subject regarding his prescribed moment-to-moment movement rate to be maintained/adhered to.

According to an aspect of the invention, an MT paradigm (such as a TT paradigm) prompts bouts (episodes) of slower movements interspersed with bouts of faster, more explosive movements. These changes in the prescribed (displayed) movement speed appear unpredictable in both the duration and the magnitude of the movement speed(s) prompted. This appearance/perception of randomness challenges the subject's cognitive reserves as well as motor prowess in a manner more challenging than reaction-based sports employing avatars to elicit the desired movement rates.

According to aspects of the invention, an MT paradigm acts to create a number of opportunities (sample points) during each test session to assess the subject's maximal movement performance. This is accomplished by prompting a series of maximum or near maximum efforts interspersed with period of lesser demands that may aid the subject in partially recovering his stamina. These "spontaneous" changes in movement speed and direction is analogous to the demands of reaction-based sports.

According to an aspect of the invention, an MT paradigm imposes (enforces) a movement strategy enabling the performance of each leg to be individually and accurately assessed. This acts to simultaneously and synergistically contribute to MT paradigm's cognitive demands that are imposed on the subject. And to also characterize the performance of each leg individually.

According to an aspect of the invention, in an MT paradigm (such as a TT paradigm) the subject is instructed to "shuffle" when responding to visual cues, i.e. push off the back leg while stepping with the front leg, i.e. the leg closest to the displayed virtual target/destination.

According to aspects of the invention, an MT paradigm is configured to more fully challenge the subject's sensory, cognitive and neuromuscular systems than other known systems.

An aspect of the present invention is the recognition that persons moving within their environment, whether athletes on the field or court or geriatric patients ambulating across their room, must, based on visual observation, navigate/negotiate their movement path. And in many cases, they must also simultaneously "modulate/control," either consciously or subconsciously, the rate in which they so move. These two distinct challenges are requisite to arriving at the correct direction at the correct time, and are consistent with the definition of a DT (or TT or MT) paradigm.

According to an aspect, the present invention challenges cognitive function, which is measured via reaction time and the resulting "correctness" (compliance with) of both the distance and direction the subject elects to move to satisfy the visual cues dictating the prescribed movement rate and direction. The present invention elicits movement from the subject that more accurately replicates/simulates the type of three-dimensional movement of real sport; movement that is more complex than the "postural control" practiced in tests of static balance.

According to an aspect of the invention, improved DT (or TT or MT) paradigms assist in managing exercise programs to detect signs of overtraining and heightened risk of orthopedic and/or brain injury.

According to another aspect, the present invention exploits sport simulation incorporating a MT ("divided attention") paradigm that more profoundly challenges the athlete's sensory, cognitive and motor prowess, resulting in enhanced measurement sensitivity and relevance for exercise prescription management and injury prevention.

According to a further aspect of the invention, a method of evaluating a subject, the method including: prompting shuffle-step movement of the subject, wherein the prompting includes prompting the subject to make a series of translations of varying length and direction; during the movement, directing the subject to obtain a series of varying target levels of intensity of movement, with the target levels of intensity conveyed to the subject; and enforcing the shuffle-step movement of the subject prompted by the prompting, wherein the enforcing includes detecting movement of the subject in which one leg of the subject crosses in front of the other leg of the subject. The prompting includes displaying on a screen, which is visible to the subject during the shuffle-step movement, a target that indicates where the subject is to move, wherein the target is moved on the screen from one location to another as each of the translations is completed.

According to an embodiment of any paragraph(s) of this summary, the displaying includes displaying the target in various locations in a representation of a physical area in which the subject moves.

According to an embodiment of any paragraph(s) of this summary, the method includes displaying on the screen a virtual representation of the subject that moves within the representation of the physical area in response to movement by the subject.

According to an embodiment of any paragraph(s) of this summary, the translations of the subject are completed when the virtual representation of the subject intersects the target.

According to an embodiment of any paragraph(s) of this summary, all of the translations in the series of translations does not exceed 30 feet in length.

According to an embodiment of any paragraph(s) of this summary, the directing also includes varying duration of the varying intensities of movement, such that both the level of intensity and the duration of individual levels of intensity both vary during different of the translations.

According to an embodiment of any paragraph(s) of this summary, the target levels of intensity are varied in durations of 10 seconds or less.

According to an embodiment of any paragraph(s) of this summary, the directing includes displaying a symbolic representation of the target level of intensity, with the symbolic representation displayed on a screen that is visible to the subject during the shuffle-step movement.

According to an embodiment of any paragraph(s) of this summary, the prompting includes displaying on the screen a target that indicates where the subject is to move, wherein the target is moved on the screen from one location to another as each of the translations is completed.

According to an embodiment of any paragraph(s) of this summary, an exercise intensity of the subject is also displayed on the screen.

According to an embodiment of any paragraph(s) of this summary, the method further includes providing notification to the subject when the subject deviates from the target intensity by more than a predetermined amount.

According to an embodiment of any paragraph(s) of this summary, the providing notification includes providing visual notification on the screen.

According to an embodiment of any paragraph(s) of this summary, the method further includes tracking position of the subject during the movement.

According to an embodiment of any paragraph(s) of this summary, the method further includes characterizing one or more aspects of movement of the subject.

According to an embodiment of any paragraph(s) of this summary, the characterizing includes determining a measure of compliance of the subject with shuffle-step movements at target levels of intensity.

According to an embodiment of any paragraph(s) of this summary, the characterizing includes determining a reaction time of the subject, and further including comparing the reaction time with a baseline reaction time of the subject.

According to an embodiment of any paragraph(s) of this summary, the characterizing includes determining one or more of a reaction time of the subject, an acceleration of the subject, and a deceleration of the subject; and further including comparing the reaction time with a baseline reaction time of the subject, the acceleration with a baseline acceleration, and/or the deceleration with a baseline deceleration.

According to an embodiment of any paragraph(s) of this summary, the characterizing includes determining an acceleration of the subject, and further including comparing the acceleration with a baseline acceleration of the subject.

According to an embodiment of any paragraph(s) of this summary, the characterizing includes determining a deceleration of the subject, and further including comparing the deceleration with a baseline deceleration of the subject.

According to an embodiment of any paragraph(s) of this summary, the enforcing includes providing the subject with feedback when the one leg of the subject crosses in front of the other leg of the subject.

According to an embodiment of any paragraph(s) of this summary, the providing includes displaying visual feedback on a screen that is visible to the subject during the shuffle-step movement.

According to an embodiment of any paragraph(s) of this summary, data gathered during a translation in which the one leg of the subject crosses in front of the other leg of the subject, is not used in characterizing movement of the subject.

According to an embodiment of any paragraph(s) of this summary, the prompting, the directing, and the enforcing occur continuously throughout a test duration of 1 to 20 minutes.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

The annexed drawings, which are not necessarily to scale, show various aspects of the invention.

FIG. 13 is a first page an example assessment result for a user.

FIG. 14A is a first part of a second page of the example assessment result.

FIG. 14B is the second part of the second page.

FIG. 15 is a table of example normative ranges for assessment data.

DETAILED DESCRIPTION

Figure 1:
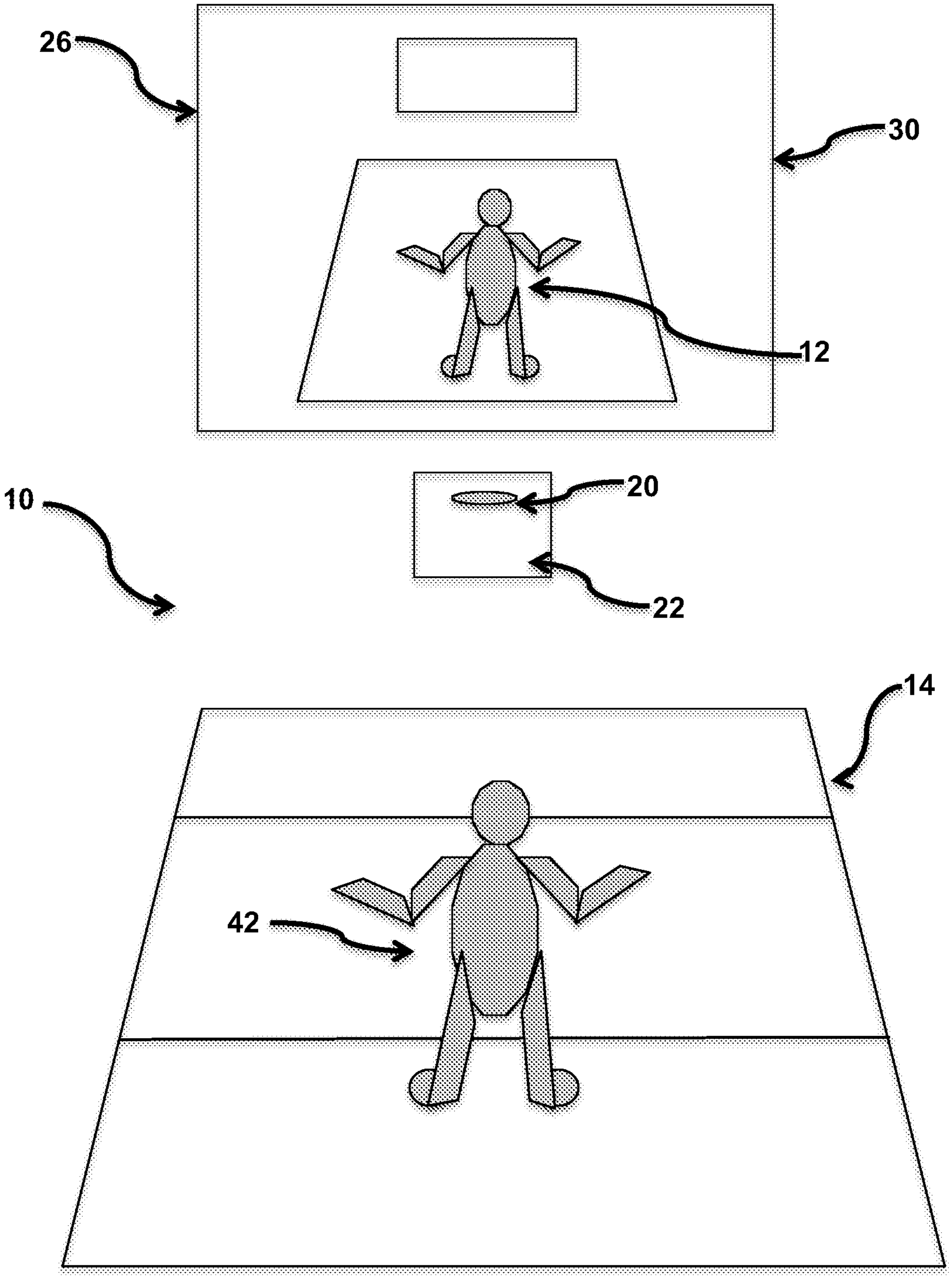
FIG. 1 is an oblique view of a system in accordance with the present invention.

Multi-task (MT) paradigms may be used to evaluate a subject in a recreation of cognitive and motor/movement challenges inherent in dynamic environments, such as those encountered during sports. Such paradigms provide multiple tasks that the subject must engage in at the same time. MT paradigms include dual-task (DT) paradigms, in which the subject engages in a task that requires the subject to perform two tasks simultaneously, and triple-task (TT) paradigms, in which the subject engages in a task that requires the subject to perform two tasks simultaneously.

Known DT (other MT) paradigms fail to recreate the cognitive and motor/movement challenges inherent in dynamic environments that include reaction based sports such as football, basketball and similar. Nor do known DT (and other MT) paradigms provide the metrics/analytics to characterize a subject's cognitive and motor capabilities under "game conditions." For data that may improve detection of a subject's increased risk of orthopedic injury or of overtraining syndrome.

Reaction-based sports challenge the athlete's/subject's cognitive, sensory, and neuromuscular systems. These three systems must be assessed concurrently. There is considerable research that supports this concept. Functional performance in such tasks is the observable end result of the interaction of muscular, sensory, and cognitive system processes. Performance in sport requires simultaneous processing of cognitive, sensory, and motor information.

The relative change in performance associated with dual-tasking is referred to as dual-task interference or the dual-task effect (DTE). Individuals with neurological deficits may be particularly susceptible to dual-task interference, because the relative increase in attentional demands to control motor performance means that there are fewer attentional resources available for simultaneous performance of secondary tasks.

Many past attempts at MT paradigms for evaluating athletes and other subjects challenged on multiple levels has been relatively crude. In one study the subject read a word printed on a sign out-loud while ambulating across a room. Other known DT paradigms have the subject walking up stairs while tasked with counting down by 3s out loud. Such examples of DT paradigms appear to have little fidelity with reaction-based sports and other dynamic environments.

An improved DT or TT paradigm, one with improved measurement sensitivity, novel analytics in addition to greater fidelity with dynamic real world environments may improve the detection of symptoms of overtraining syndrome, and the increased risk of orthopedic and brain injuries. It may also contribute to the rehabilitation process for both assessment and rehabilitation, as well as for performance enhancement and assessment tool for healthy populations.

Some embodiments below involve the use of an interactive or "virtual" simulator, such as that described in U.S. application Ser. No. 14/077,619, filed Nov. 12, 2013 (the drawings and description of which are incorporated herein by reference), to challenge the subject's cognitive, sensory and motor capabilities by simulating the challenges of physically demanding work environments, as well as the activities of daily living for physically compromised/aging populations (among many other possibilities).

Embodiments described herein differ from known DT paradigms in a number of fundamental ways including the introduction of an exertional (aerobic and anaerobic) component to challenge the subject's cardiorespiratory system. The embodiments act to elevate the subject's heart rate to those experienced in reaction-based sports by prompting the subject to respond to spontaneous 3-dimensional movement cues. This is in sharp contrast to DT paradigms that display placards (signs) whose content is to be read out loud, i.e. the Stroop Test as the subject walks by those signs.

The scope of the present invention is not limited to athletic populations, but rather may benefit most weight bearing populations. Persons moving within their environment; whether athletes on the field or court or geriatric patients ambulating across their room, must, based on their visual observation, endeavor to safely navigate their movement path. And in many cases, they must also simultaneously "modulate/control", either purposely or subconsciously, the rate at which they move.

DT Paradigm, First Embodiment

By way of example, a football running back carrying the ball will continuously select a movement path, based on his visual observation, that offers the best opportunity to gain maximum yardage. At times, the player may also modulate his forward speed to elude tacklers or "wait" for his blockers to "clear" his path. The same paradigm may apply to a basketball player driving to the basket to score. Or the senior citizen avoiding her cat as she moves from the sink to the table.

The graded test described in U.S. application Ser. No. 14/077,619 (the '619 application) was to replicate the uniform, predictable progression of exercise intensity employed with treadmill cardiac stress tests. It was unexpectedly discovered that this graded test also enabled a novel and remarkably efficacious DT paradigm (divided task). One that more precisely replicates real world challenges/tasks than known DT paradigm methodologies. It also generates previously unavailable data/analytics with clear benefits for improved assessment of broad weight bearing populations.

This first embodiment incorporates the graded protocol taught in the '619 application. As will be discussed in further detail this dual task paradigm embodiment provides visual cues that prompt the subject to move progressively faster in a predictable fashion while simultaneously moving to the correct targets. Like driving a car, the subject must continually follow the prescribed path and must also maintain the "displayed" movement speed as it progresses. Over time, the subject's ability to successfully achieve increasingly more challenging stages (levels) of performance delivered by the present invention's dual-task paradigm may provide objective evidence of improvement in their recovery or other outcomes of interest.

The subject's percentage time in compliance, the degree of compliance, as well as other metrics discussed below can be compared to either established normative data or the subject's previous assessments to assist in determining performance trends that may illuminate actionable or non-actionable performance differences or deficits. Peak heart rate, movement speed and Work Rate (METs, etc.) achieved could then be compared to the subject's DT performance to provide the estimated cost of the single task vs. a DT paradigm.

This method of progression is analogous to a treadmill graded test that acts to progressively increase the work rate in a predictable manner to the subject. The subject's peak performance, such maximum running speed is only known at near termination, i.e. failure. The subject's efforts up to this time may serve as a warmup, among other factors. Similarly, in this embodiment the subject's movement performance is typically maximal only at near the subject's termination (exhaustion) point. Such maximal performance-related data can be invaluable to determine progress and existing deficits for performance enhancement, injury prevention and in rehabilitation The graded test taught in the '619 application is used to create a novel DT paradigm by prompting a subject to move moment to moment at the prescribed movement rate to virtual targets that correspond to physical locations in the real world. This graded test displays to the subject visual cues that are predictable in that these cues prompt subject movement at progressively faster movement rates, thereby progressively and predictably increasing the subject's work rate until termination.

In this first embodiment the subject may be instructed in advance that the movement rate will progressively increase until termination either volitionally due to fatigue, or compulsory because of the presentation of symptoms or other factors. The subject's compliance with this progressive increase in the prescribed movement rate may serve as an indicator/marker of the subject's cognitive and physical response to the cognitive and physically demanding components of this novel DT paradigm. The percent time in compliance and the degree of compliance as well as other metrics can be compared to either previously collected normative data or previously administered assessments of the subject to assist in determining trends that may indicate actionable or non-actionable performance differences/deficits.

This novel DT paradigm demonstrated improved fidelity with reaction-based sports and other physically challenging environments, generating previously unavailable analytics to assist in the detection and characterization of symptoms of Overtraining Syndrome (OTS), increased risk for orthopedic and brain injury, as well as maladies that have the potential to diminish one's navigational/movement capabilities.

There are material differences between the graded test that enable a novel DT paradigm that distinguish it from known prior approaches. In contrast to many DT paradigms that present visual and/or auditory cues/tasks that are episodic (sporadic/periodic) in their presentation, the graded test presents visual cues that are typically continuous in their delivery. This novel DT is somewhat analogous to driving a car where the driver must maintain the prescribed speed limit as well as continually point the car in the correct direction. These two distinct challenges require essentially constant cognitive involvement on the part of the driver; for example, a fatigued or intoxicated driver may find execution of such a divided task quite challenging and even dangerous as it requires maintenance of concentration and diligence.

With the present invention's DT paradigm, two distinct, but related visual cues create a DT paradigm that more precisely replicates real world challenges. This DT paradigm is by its very nature analogous to a subject's ability to successfully navigate his or her environment, regardless of whether the subject is a geriatric patient, a wounded warrior, or a competitive athlete. In addition it generates unprecedented data via the ability of position tracking movement capabilities to simultaneously measure the subject's moment to moment full body physical response. In contrast to DT paradigms that present visual and auditory cues/tasks that are episodic in nature, such as the subject's reading of a sign (i.e. the Stroop Test) as the subject walks by, or the subject stands on a static balance device, the present invention presents visual cues that are continuous in their delivery, multidirectional, and are, by their very nature, fundamental to the ability of a subject to successfully navigate his or her environment where multidirectional movement is required.

This novel DT paradigm assess two fundamental capabilities inherent in this protocol: 1) the subject's assumption and maintenance of the correct movement distance and direction, and 2) the maintenance of the prescribed movement rate through execution of the protocol. These DT paradigm assessments could be repeated periodically to determine changes from a baseline test and/or normative data. Assessments could be performed every few days, weekly or less frequently. Comparing the results of such periodic assessments over time can provide objective data regarding the subject's performance capabilities, which may become compromised if the subject is presently suffering a state of overreach or overtraining, or if the subject has other types of impediments, such as orthopedic or neurological, to successful, safe and effective movement. The subject's performance on the aforementioned assessments could also be compared to relevant normative data or a "healthy" baseline test when the subject was not suspected of suffering from Overreaching and/or Overtraining. Or for detecting a heightened risk for injury. This novel DT paradigm can be used to document the athlete/subject's current status relating to their training or rehabilitation, thereby assisting in determining the degree of recovery and/or progress for improved management of exercise prescriptions. This novel data may also contribute to concussion management programs as well as orthopedic injuries or diseases.

For program management, DT paradigm ("Divided Attention") may deliver an appropriate 3-6 minute (or alternatively 3-8 minute) programmed warm-up that may elicit from the subject abrupt, aggressive changes in movement speed and perhaps movement direction that act to more profoundly challenge the subject's sensory, cognitive, cardiorespiratory and musculoskeletal systems. These periods of time are merely examples, and a variety of other warm-up times (longer or shorter) may be used as alternatives.

Thus this invention serves to measure a subject's performance capabilities as well as detect any movement performance abnormalities and weaknesses that may be material to the subject's recovery for the management of fitness, performance enhancement or rehabilitation programs.

The DT paradigm may calculate the accumulated time that the subject remained in compliance with the prescribed movement rate and also moved in the correct direction, i.e. the total time the subject was moving at the prescribed rate and prescribed direction. For example, assume that the duration of the assessment was 7 minutes, 34 seconds (7:34) before termination, and that the subject was in compliance with the prescribed movement speed for 3 minutes and 14 seconds. The percent time in compliance could be calculated as a percentage of the total time for example. This percentage of time in compliance can be compared to previous assessments or to normative data. For example purposes only, a healthy athlete may be in compliance for 78% of the assessment time, compared with 47% of the assessment time when the athlete is suspected of being in a state of Overtraining or exhibiting signs of an orthopedic issue. And the subject's movement data under higher stress movement scenarios may be revealing of asymmetrical movement patterns that may indicate a training effect, the presence of an injury, etc. by eliciting higher levels of cognitive and physical stress. This data could be presented in a graphical format with Time along the X axis and Percent Compliance along the Y axis. One plot (line) would represent perfect compliance and a second line would represent the subject's actual (measured) compliance. The difference between these lines may illustrate/document the degree of non-compliance with the assessment protocol.

Also calculated and presented may be a comparison between the subject's time in compliance at various prescribed movement rates. By way of example it may illustrate/depict that the subject was in compliance 67% of the time at slower movement speeds in contrast to 39% of the time at higher speeds.

The number of vector directions that may be reported may include as few as two to as many as 8 or more.

The DT paradigm assessments described above may be performed to establish a healthy baseline, i.e. when the subject is not in an overtrained state, or to assist in establishing whether an apparently healthy subject is free of orthopedic injuries or similar. They may also be used to track improvement in a rehabilitation program of any nature, or the degree of regression during a chronic illness.

The graded exercise test measures both functional cardiorespiratory and kinetic (movement) performance. It provides a novel, objective outcome measure of the subject's global performance capabilities. Data that is uniquely relevant to the patient, physical therapist, physician and trainer.

This DT task paradigm simultaneously challenges the subject's muscular, sensory, and cognitive systems for a more actionable and functional measurement of performance. It also challenges the cardiorespiratory system to assist in determining the subject's capacity to successfully and safely resume daily activities. In a realistic context, this DT paradigm assesses performance of the complex tasks. Cardiac function is measured during interactive, 3-dimensional movements in real-time settings. Measurement of reaction time and decision-making skills is made possible by the presentation of spontaneous visual cues, in sharp contrast to the predictability of preplanned tests. To characterize "kinetic" health, the present invention measures and reports moment-to-moment reaction time, acceleration, speed, deceleration and distance traveled in each movement vector. Physiological parameters measured and reported include heart rate by telemetry and work rate expressed as METs.

The present invention characterizes exercise capacity (cardiorespiratory status) by reporting in "metabolic equivalents" (METs). Heart Rate response to increasing work is reported. Heart Rate and Work Rate provide novel and meaningful data regarding the subject's heart rate at each work rate during the test. If, for example, the subject's heart rate at a given work rate is exaggerated or blunted, it will be clearly evident. Heart rate and work rate provide novel and meaningful data regarding the subject's heart rate at each work rate during the test. If, for example, the subject's heart rate at a given work rate is exaggerated or blunted, it will be clearly evident.

Measured degradations in the aforementioned measurements in comparison to a previous baseline test and/or other prior subject assessment(s), or to normative data may be indicative of a state of overtraining, increased risk of injury or other undesirable states/conditions.

Reaction time versus time is or may be reported and/recorded, for example in hundredths of a second: the test described above measures the elapsed time from the presentation of the visual cue until the initial movement in the correct direction. Reaction time is or may be averaged for 30 second time periods and displayed as a plot versus time, or using "cycling" of the prescribed movement rate and direction. Aligning these values alongside the METs vs. time curve may allow determination of the effects of progressive work efforts on the subject's ability to react. The measurement of reaction time may show the degradation of attention span, and is cited as a key indicator of a subject's propensity to fall in geriatric populations.

The scope of the present invention may not be limited to sports, but rather all weight-bearing populations. Note that the present invention may also be applicable to certain wheelchair-bound populations as well. Populations ranging from those suffering brain injury or disease to movement disorders in geriatric populations all benefit from the introduction of multiple sensory challenges that challenge (or test or strain) the subject's capabilities, and assess the subject's processing power (cognitive reserves) as well as physical movement performance. As previously discussed, the accumulative effects of training and competition place the athlete periodically in the state of overreaching, accompanied by risk of overtraining, resulting in diminishment of the athlete's performance capabilities; i.e. "disruptions in multiple physiologic systems." Diminishment of performance may place athletes at increased risk of brain and orthopedic injury as a result of overtraining, for example.

Characterizing whole body recovery/response to the current DT paradigm provides previously unavailable critical data to more effectively manage the stress-regeneration cycle as well as detect heightened risk for orthopedic or brain injury. In contrast to tests not accounting for the influence of increased metabolic activity, the present invention's continuous measurement of heart rate and movement speed at progressively higher metabolic rates characterizes the subject's work capacity. And reaction time to spontaneous visual cues assesses cognitive function under game conditions. Such assessments generate previously unavailable data regarding the status of the athlete's stress-regeneration cycle for the purpose of reducing the risk of injury resulting from the modifiable degradation of sport-specific performance capabilities. To provide a novel marker of whole body recovery for exercise prescription management. Diminishment of reaction times and accelerations, as well as an exaggerated heart rate for a given work load compared with baseline tests may expose (detect) early fundamental signs of increased risk of overtraining.

This paradigm elicits subject responses to cognitive challenges at varying metabolic (work) rates (these prompted work rates are typically unpredictable to the subject) to objectively document increasing physical stress on cognition (as measured by reaction time and movement accuracy) and well as the resulting effects on the subject's accelerations, movement speed, decelerations in a variety of movement vectors that may range from as few as two to as many as eight movement vectors.

The visional cues/prompts act to simulate the cognitive and physical demands of reaction-based sports that include the abrupt/violent changes in direction as an athlete responds to game play. For example, a football defensive back responds moment-to-moment to the receiver that he is guarding. The resulting characterization of the athlete's whole body response to simulated game play provides a novel measure of the accumulative potentially deleterious effects of training and competition. Unlike the results of currently available tests of isolated capacities, this approach more accurately characterizes real-world performance, eliciting information that is directly transferable to reaction-based sports and other potentially physically demanding environments.

The progressive increase in Work Rate, which is derived from the movement rate of the subject, measured in METs or equivalent, can also serve to gauge the subject's response to more physically demanding dual tasks. With this embodiment this progressive increase in the prescribed movement is known to the subject. The aforementioned prompting is accomplished by the appearance of virtual targets that correspond with locations in the real world. This presentation of two distinct, but related tasks creates a novel DT paradigm.

Applications range from, but are not limited to, healthy athletic populations to weight bearing geriatric populations as well as orthopedic and neurological rehabilitation. Some example applications include: screen for early signs of overtraining to more effectively manage exercise prescriptions; detect movement deficits to improve performance and reduce the risk of orthopedic injuries; assist in ensuring satisfactory return from injury; gauge sport-relevant cardio respiratory fitness; and personalize training programs according to each subject's exercise tolerance.

The DT paradigm can characterize the subject's ability to successfully navigate his or her environment based on visual observation, regardless of whether the subject is a geriatric patient, a wounded warrior, or a healthy or injured athlete. There is a clear distinction regarding how this embodiment progressively increases the subject's movement rate and known movement-oriented video games. Interactive fitness video games typically control the player's movement rate by modulating/controlling the rate at which visual movement cues/prompts are presented to the player via the display. For example, if the objective of an interactive fitness game is to prompt the real world player/exerciser to move faster in a given vector direction, the virtual game cues/prompts may therefore move correspondingly faster in this desired movement direction. Accordingly a virtual tennis game designed for the Microsoft Kinect may prompt the real world player to move in a manner analogous to real world tennis, i.e., the virtual tennis ball would be "placed"/"hit" to the area the real world player is to be "relocated."

In sharp contrast, the approached described above (for example using what is disclosed in the '619 application) is distinct from the aforementioned approach in that the displayed (prescribed) movement rate is independent of the rate at which the virtual targets/designations are displayed. For example, the virtual targets may appear and reappear at high or low frequency in a variety of locations in the virtual world, while the rate at which the subject is prompted to move to said virtual targets is governed solely by the interactive sports simulator taught in '619 displayed movement speed meter. To follow a protocol/assessment the subject must be attend to two distinct tasks, with the result a novel DT paradigm.

DT Paradigm, Second Embodiment

In contrast to the first embodiment, this second embodiment provides visual cues that prompt movement rates that may appear to the subject to either be unpredictable or predictable in duration as well as magnitude of the speed prompted. This appearance of randomness acts to further challenge the subject's cognitive prowess (reserves) as well as placing additive stress on the subject's movement capabilities. This is another variation of this the DT paradigm that, in addition to prompting a predictable progression of the subject's movement rate, may also prompt movement rates of varying speeds that may appear unpredictable to the subject. In other words, the subject may be prompted to move faster or slower as the protocol progresses and in a manner that appears to the subject to be unpredictable.

This second embodiment acts to progress (change) the subject's movement rate in what appears to be unpredictable fashion. The subject may be challenged via bouts (episodes) of slower movements interspersed with bouts of faster movement efforts. The changes in the prescribed movement speed may appear to the subject to either be unpredictable or predictable in both the duration and the magnitude of the movement speed prompted. This appearance/perception of randomness may further challenge the subject's cognitive and motor prowess (reserves). This periodic modulation of the prescribed speed in a pseudo random manner (or either equal periods or varying periods) is believed to necessitate greater concentration/focus on behalf of the subject. The subject's actual compliance with this novel DT paradigm may be compared to "perfect" compliance; a score representing the difference over time between the subject's actual degree of compliance and a perfect level of compliance. The subject's score could also be compared to normative data and/or previous tests by the subject.

This second embodiment differs from the first embodiment described above in that the first embodiment may only create an opportunity to assess the subject's maximal effort only when the subject is near or at the point of volitional termination. In contrast, this second embodiment may create a number of opportunities to assess the subject's maximal performance status; this is accomplished by prompting a series of maximum or near maximum efforts by the subject interspersed with period of lesser demands that may aid the subject in regaining his stamina. This unpredictably from the perspective of the player is analogous to actual game play. The availability of a larger number of samples (in a single test or testing in a single session) of the subject's near maximum or maximum efforts is believed to provide for more sensitive and accurate protocol for the detection of movement deficits; deficits that may be masked at lower movement rates (stress levels) but become evident at higher stress levels.

To further increase the visual, cognitive and movement (motor) challenges, in contrast to the aforementioned predictable progression of the exercise intensity that may be known in advance by the subject, this second embodiment may deliver movement cues to the subject that are not easily predictable or anticipated by the subject. For example, the prescribed movement rate may vary in ways that include prompting changes in the pace of movement-prompting either faster movement rates or slower movement rates. Such prompting could also include prompting in a manner that may be either predictable or unpredictable to the subject. Also the duration of any such slower or faster movement pace may be predictable or unpredictable to the subject. These changes in movement pace or direction may become "explosive" to mimic the cognitive and motor stresses of actual reaction-based sports.

It is believed that the aforementioned combinations of predictable and/or unpredictable prompting of variations in the prescribed speed may require greater concentration/focus on behalf of the subject in order to remain compliant with the prescribed movement rate. And that it will produce higher physical stress levels, that may detect movement deficits that relate to the health and conditioning of the subject's knees and ankles. As such, this prescribed apparent (pseudo) randomness may further challenge the subject's cognitive prowess (reserves); it may also act to increase the subject's physical performance challenges as the subject may be subject to frequent and aggressive changes in movement direction and speed which may appear to the subject as unpredictable. This protocol may be analogous (similar) in its cognitive and physical demands to those of a defensive player guarding his/her offensive opponent, where the defensive player must react (anticipate and react) to the offensive player's actions.

The following teaches how this DT paradigm "abruptly" challenges the subject's movement capabilities to further improve measurement sensitivity and novel analytics. Though an important application for this presents invention is sports/athletics, this protocol is applicable to populations that include geriatrics (aging populations), orthopedic and neurological patients. For these populations the amplitude (the work rates) are sufficiently dampened to so accommodate.

The imposed abrupt or "violent" (sudden) changes in movement direction provide many more opportunities for sampling the key measurements discussed herein. A traditional graded test, whether implemented via a treadmill or with the present invention (sports simulation) challenges the subject (i.e. elicits maximal effort) in many cases to make a maximal effort, for the test duration to approach or reach a state of volitional termination by the subject; that point in time that the subject is making a maximal efforts. With the second embodiment of the present invention, the subject is prompted to undertake maximal accelerations, decelerations et al periodically (sporadically) throughout the protocol/test. The result is more samples/data points to process.

System for MT Paradigms

With reference now to FIG. 1, in the system 10 the athlete's perceptual (sensing) ability is not tested in isolation, but rather as the initial stage of a continuum of capabilities ranging from the ability to recognize and interpret sport-relevant visual information, to the ability to adeptly execute, when desired, in a kinematically correct manner. The athlete's visual and cognitive skills are challenged by sensing and responding to sports simulations that demand the athlete undertake the "correct" pursuit angle. The approach described herein uniquely challenges the athlete's sensory, vestibular (balance) and orthopedic systems. With the system 10, the athlete responds with rotations, translations and vertical changes of body position to undertake the "correct" pursuit angle. This pursuit angle is known to the system 10. Unlike static balance tests, aspects of depth perception, dynamic visual acuity, peripheral awareness and anticipation skills are assessed during realistic movement.

Also material to test validity is the unpredictability of the stimuli delivered to the athlete over multiple tests and within the same test. Randomizing software algorithms may be used to ensure that the athlete cannot correctly anticipate subsequent movement challenges. This pseudo-randomization may present varying levels of challenge, demanding very low work rate levels and minimal changes in pace for those rehabilitating, or those who are cognitively or orthopedically challenged, to demanding a very high work rate level (METs) and sharp, spontaneous changes in pace and direction of movement.

FIG. 1 shows an example of a system 10 that prompts full body movement of a person 42, in a physical space 14, which may or may not be visually delineated, and which need not have definite boundaries. Movement of the person 42 is detected and tracked by a camera or other sensor 20 in a base unit 22, which may include other components such as a processor, communication ability, data storage, etc. The camera or other sensor 20 may have an adjustable field for tracking the person 42, for example be adjustable to track in an area range from 36 square feet to 400 square feet. These sizes are only examples, and many other areas for tracking (larger or smaller) are possible. As another example, the exercise area may be 10 feet by 10 feet, for a total of 100 square feet. A display 26 is used to display a view 30 to the user 42, or to otherwise prompt full body motion to be tracked by the base unit 22. The view 30 may show an avatar 12 that represents movement of the user 42 in the physical space 14.

Figure 2:
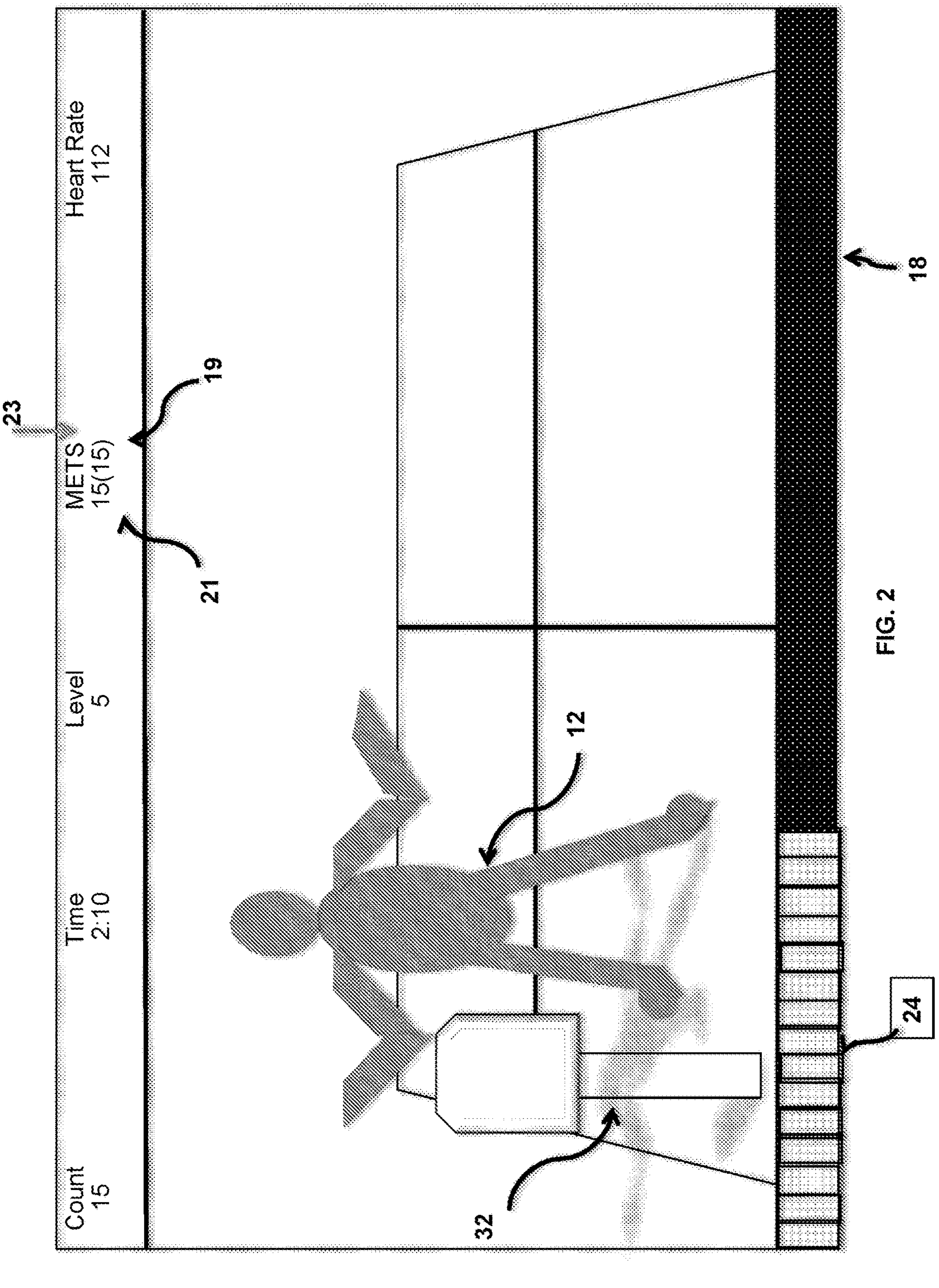
FIG. 2 is an illustration of a screen on a display device, for providing movement cues and feedback to maintain desired exercise intensity, as part of the system of FIG. 1.
Figure 3:
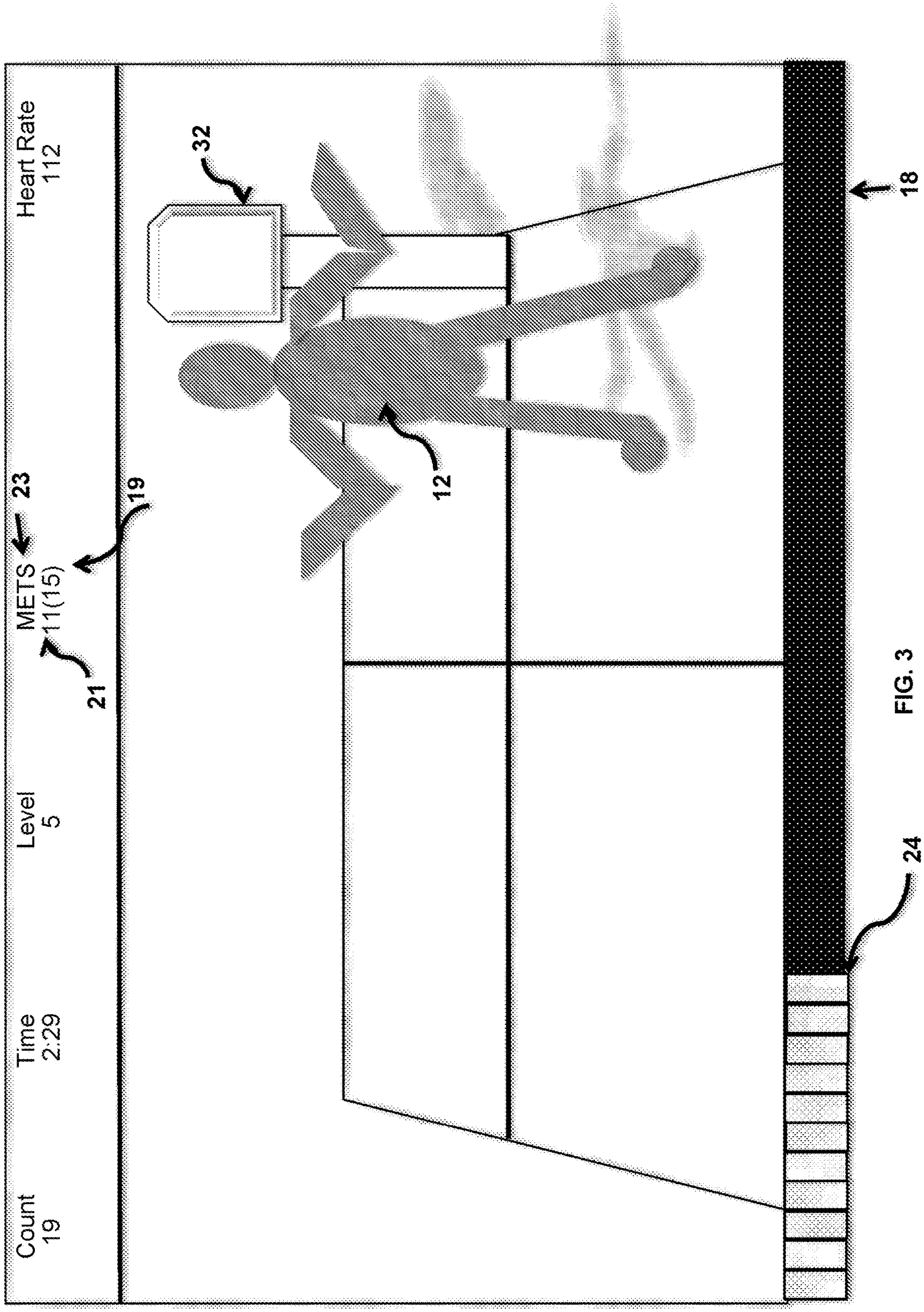
FIG. 3 is an illustration of a screen on a display device, for providing movement cues and feedback to maintain desired exercise intensity, as part of the system of FIG. 1.
Figure 4:
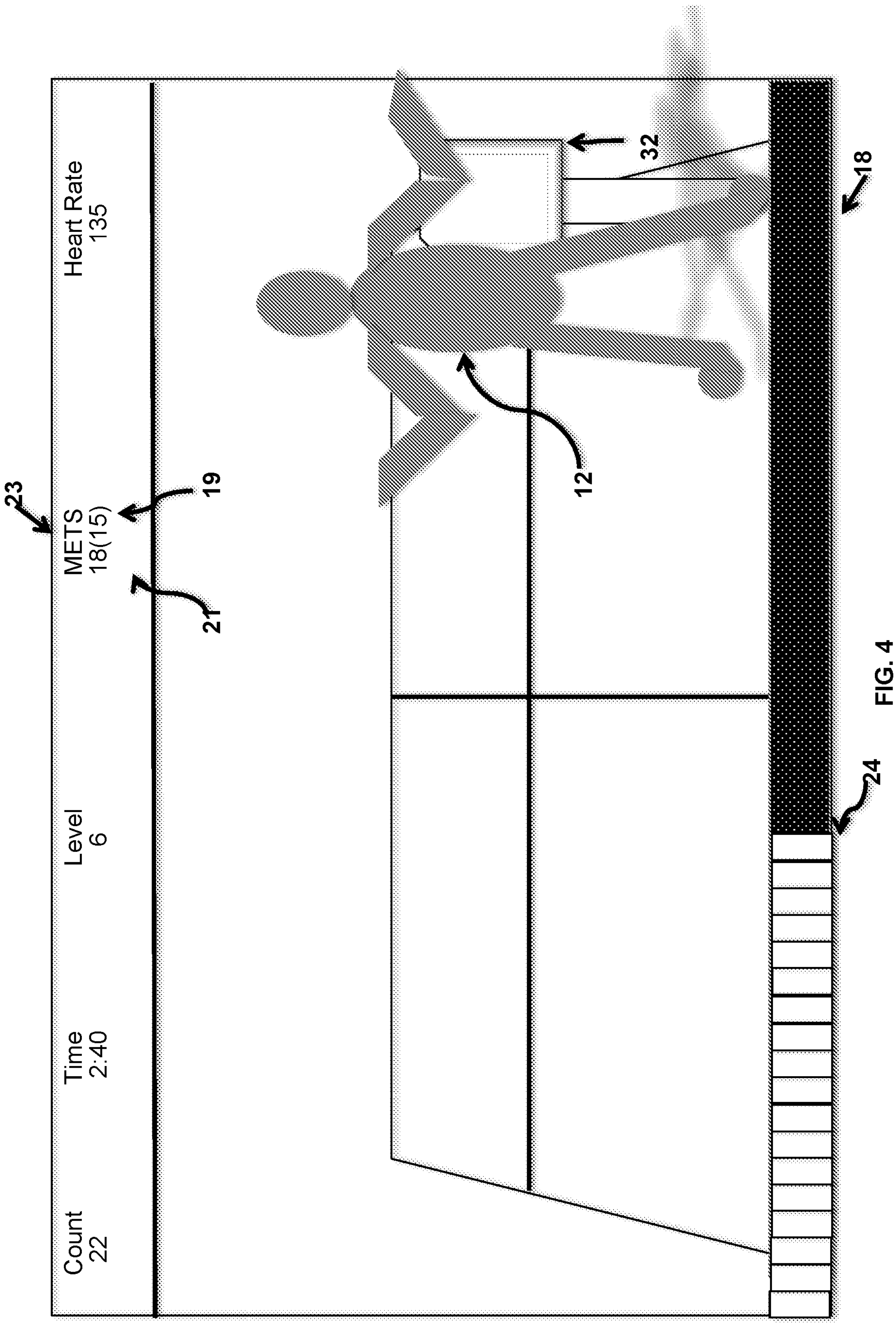
FIG. 4 is an illustration of a screen on a display device, for providing movement cues and feedback to maintain desired exercise intensity, as part of the system of FIG. 1.

FIGS. 2, 3 and 4 show two mechanisms that may be used to deliver to a test subject visual feedback regarding work rate or work load of the exercise that the subject is engaged in. In cardiac exercise (stress) tests employing a treadmill control (increase the work rate) the load is imposed on the subject by increasing the speed of the treadmill platform and/or the incline of the platform. With the increase in load, the subject needs sufficient exercise capability to assume and maintain the new work rate (load) or the test is terminated. This approach can be characterized as externally imposing the load on the subject so as to test his tolerance for exercise.

In contrast to the aforementioned externally-imposed load cardiac exercise tests, the testing described earlier herein (DT paradigms) relies on the subject's "volitional control," the subject's compliance with the prescribed work rate (the pace of the test protocol). To maintain the current pacing (work rate), it is advantageous that the subject be provided with essentially real time feedback regarding his or her performance. The feedback can be, for example, in (and/or based on) METs, calories, speed or similar metrics related to work rate. Such feedback informs subjects whether they are moving too fast or too slow.

FIG. 2 shows one example of a combination of analog 18 and digital 23 work rate meters that tell the subject his targeted work rate in METs. The digital meter at the top of the screen shows the desired METs in parentheses 19, and the METs achieved 21 to the left of the parentheses. At the bottom of the screen, an analog meter shows in lit segments a bar with the number of METs achieved 24. The meters may be provided with colors and/or textural markers, providing information to the test subject. The meter may have visual effects when the subject's work rate is outside of the desired target zone, for example flashing when the work rate is too high or too low, to act as an alert to the subject.

FIG. 3 shows another example of a combination of analog 18 and digital 23 work rate meters that tell the subject his targeted work rate in METs. The digital meter at the top of the screen shows the desired METs in parentheses 19, and the METs achieved 21 to the left of the parentheses. At the bottom of the screen, an analog meter in lit segments a bar with the number of METs achieved 24. In this example, the subject is performing at less than the desired work rate, as shown by 21 and 24.

FIG. 4 shows another example of a combination of analog 18 and digital 23 work rate meters that tell the subject his targeted work rate in METs. The digital meter at the top of the screen shows the desired METs in parentheses 19, and the METs achieved 21 to the left of the parentheses. At the bottom of the screen, an analog meter shows in lit segments a bar with the number of METs achieved 24. In this example, the subject is moving faster than the desired work rate, as shown by 21 and 24.

Figure 5:
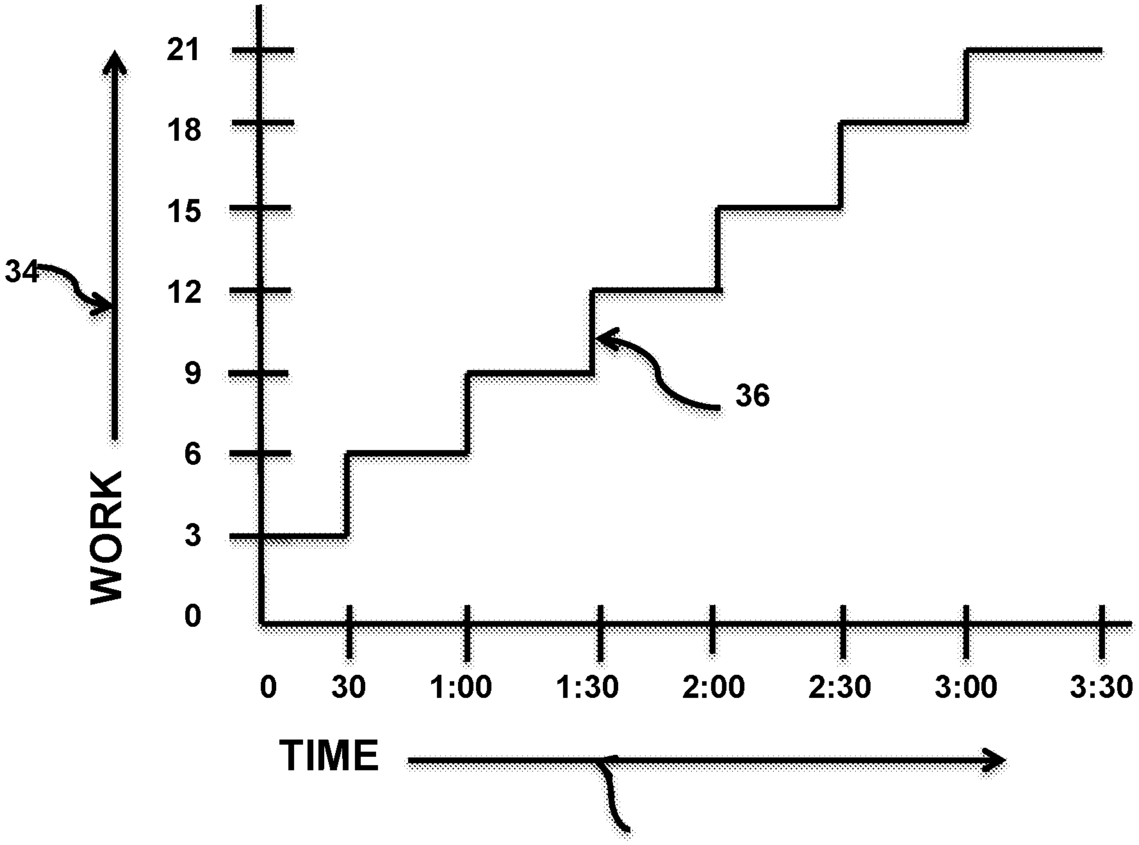
FIG. 5 shows a plot of the targeted pace of work.

The control of exercise intensity is not based on heart rate, but may be based rather on a measure of "work rate" expressed as METs derived from real time moment-to-moment positional changes in response to the system's interactive cueing, each from speed of movement during the positional changes, and distance of the positional changes. The first DT embodiment controls (modulates) the progression from low to high exercise intensity as shown, by example, in FIG. 5, wherein the work rate, shown on the Y axis, elevates by 3 METs 34 every 30 seconds 37, shown on the X axis, in this example. It will be appreciated that this is only an example value, and that a wide variety of other periods for varying the work rate may be used instead. This controlling (modulating) of the progression from low to high exercise intensity provides a controlled profile of work rate versus time, in which certain other key variables can be compared/evaluated. The exercise intensity progression can be repeated for different assessments accomplished at different times. This graded progression of exercise intensity is analogous to that of the Bruce/Balke cardiac stress tests (performed on treadmills or other stationary exercise equipment), with one major exception. The planned, one-dimensional (stationary) exercise pattern of a treadmill or stationary bike, where the subject walks/runs in place as the belt speed and angle are progressively increased, is replaced by interactive, three-dimensional movement.

By using the system 10 to analyze movement capabilities in each vector direction, it has been found that orthopedic injuries, especially lower extremity injuries, often produce movement deficits in defined movement vectors. For example, moving off an injured right knee may inhibit reaction time and acceleration when the athlete is moving to the left, and may exhibit compromised deceleration capabilities when the athlete is moving to the right. Diminished reaction time as a result of an orthopedic injury may result from deterring pain, confidence and/or loss of proprioception; additionally, acceleration/rate of force production deficits may also be observed.

The ability to perform both of the above tasks simultaneously, maintaining the work rate demanded by the meter, and at the same time, recognizing and responding to moment-to-moment cues at the correct pursuit angle, is an example of dual tasking.

Figure 6:
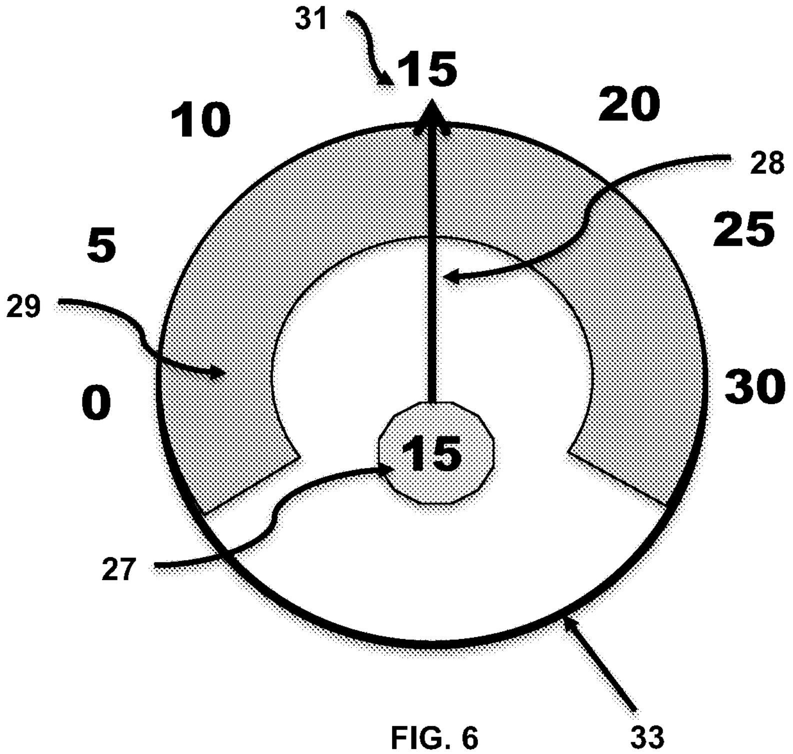
FIG. 6 is a dial-type graph that shows the prompted pace of subject's work.

As discussed herein, the second embodiment of the DT paradigm introduces unpredictability to the visual prompts. In this second embodiment of the DT paradigm, a large meter 33, an example of which is shown in FIG. 6, is prominently positioned in the view 30 (FIG. 8) in the virtual world that the subject is interacting with. The meter may be a dial, as illustrated here, or in another form that illustrates a prompted work rate. The meter 33 must have a means of displaying both the prompted work rate 27 and the moment-to-moment work rate achieved by the subject 31. In this example, the prompted rate 27 is displayed on a lit dial in the center of the meter. An arrow 28 points to the work rate achieved by the subject 31. A band inside the meter 29 may change colors or flash or otherwise provide feedback to the subject as regards his work rate. FIG. 6 illustrates a prompted work rate 27 of 15 METs 31, and the subject is in moment-to-moment compliance at 15 METs achieved.

Figure 7:
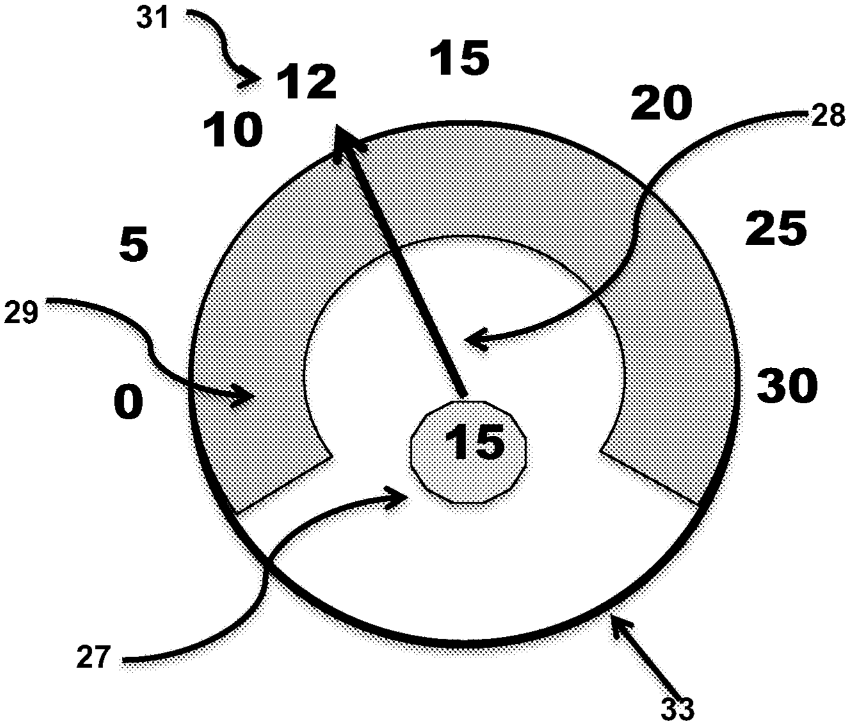
FIG. 7 is another dial-type graph that shows the prompted pace of subject's work.

FIG. 7 shows the same meter as in FIG. 6, with the same prompted rate 27, but the arrow 28 shows that the subject is working below the prompted work rate, with the subject working at the rate of 12 METs, as shown at 31. This meter is used to cue the subject to make sporadic and instantaneous changes in pace. The meter may display a demand for 15 METs in one instant, 3 in the next, causing the subject to race to one target, suddenly brake, and walk slowly to the next. This spontaneous shift in pace/demand puts realistic, sport relevant stresses on many of the subject's systems, whether cognitive, orthopedic, vestibular or cardio respiratory.

Figure 8:
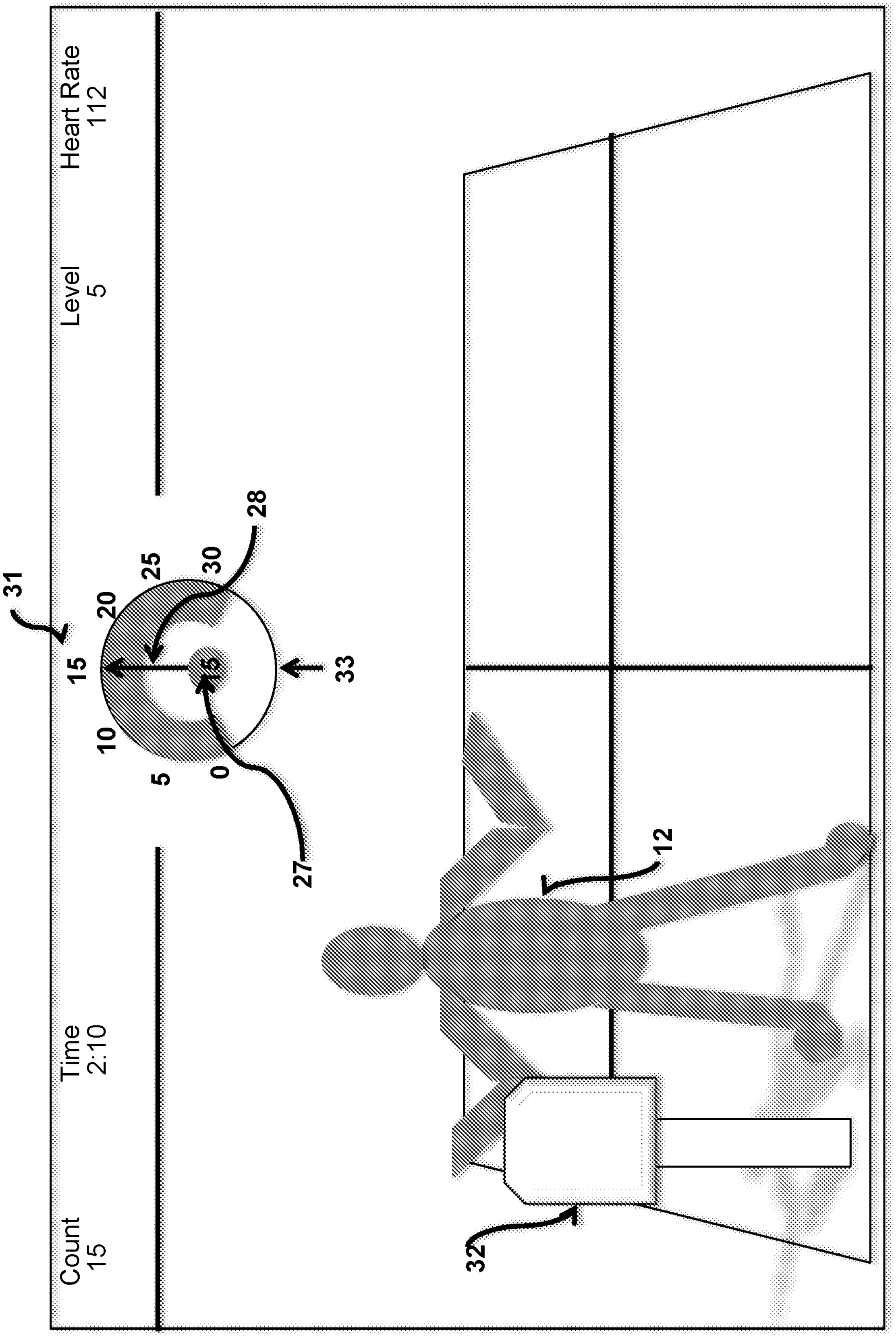
FIG. 8 is an illustration of a screen on a display device, for providing movement cues and feedback to maintain desired exercise intensity and moment-to-moment changes in location, as part of the system of FIG. 1, with the subject moving at the prompted movement rate and prescribed direction, in compliance with the system requirement.

The subject's avatar 12 on the display screen 30 moves in one-to-one correspondence to the movement of the subject in the real world 42. FIG. 8 shows that the subject's avatar 12 has reached his target/cue 32. The meter 33 displays the target work rate 27 as 15, and the arrow 28 shows that the subject 12 work rate achieved 31 matches the target at 15 METs. The dial-type meter 33 fluctuates sporadically so that the subject has to continually and intermittently stop and start and adjust his pace and his moment-to-moment location to meet the prompted pace of the meter 33. In FIG. 8 the subject is moving at the prompted movement rate and prescribed direction, and is in compliance with the system requirement.

Figure 9:
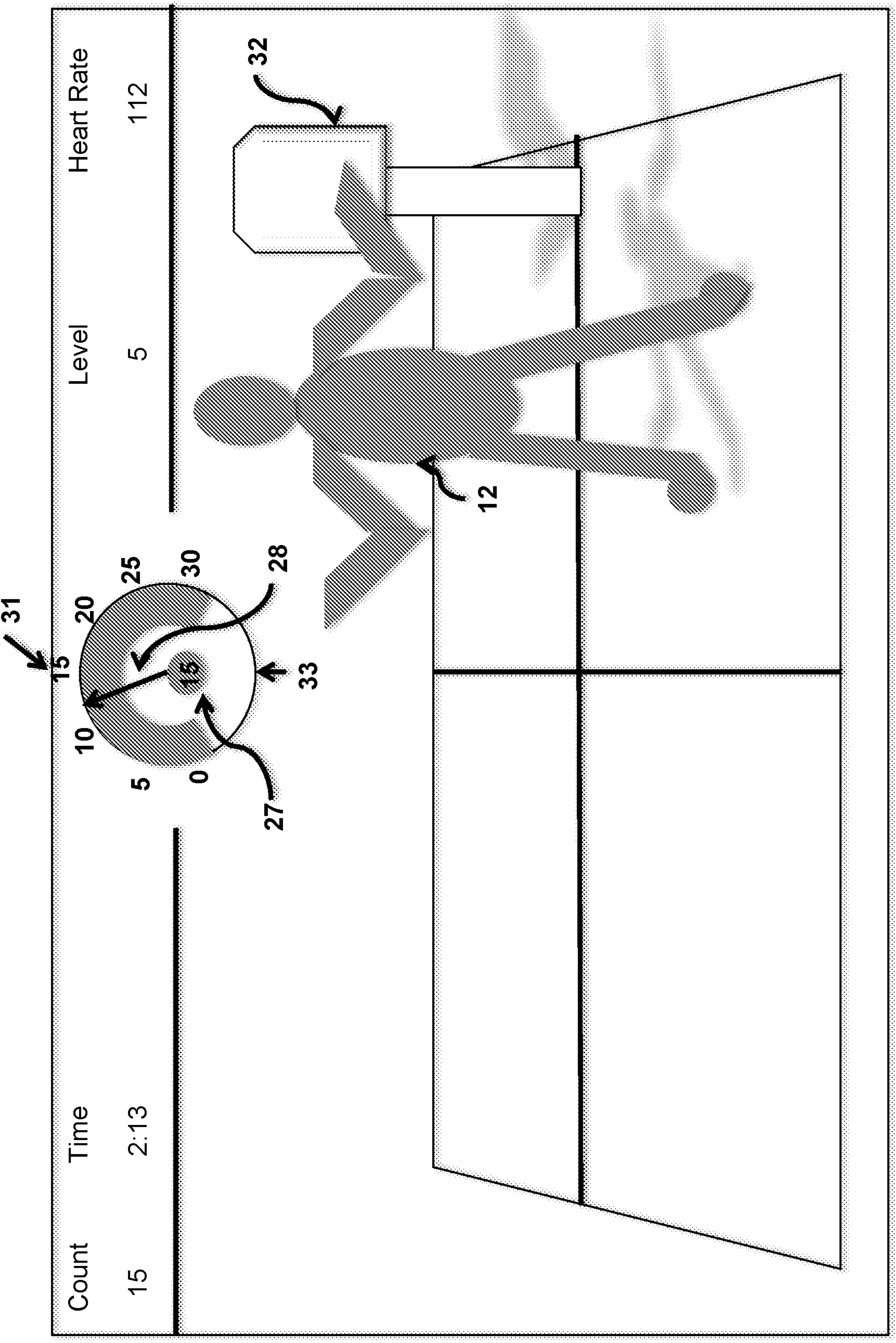
FIG. 9 is an illustration of a screen on a display device, for providing movement cues and feedback to maintain desired exercise intensity and moment-to-moment changes in location, as part of the system of FIG. 1, moving too slowly to be in compliance with the system requirement.

FIG. 9 shows that the subject 12 has slowed down in his transition to the next target 32. The meter 33 displays the target work rate 27 as 15, and the arrow 28 shows that the subject 12 work rate achieved 31 is below the target at 12 METs. This is a condition in which the subject is moving too slowly to be in compliance with the system requirement.

Figure 10:
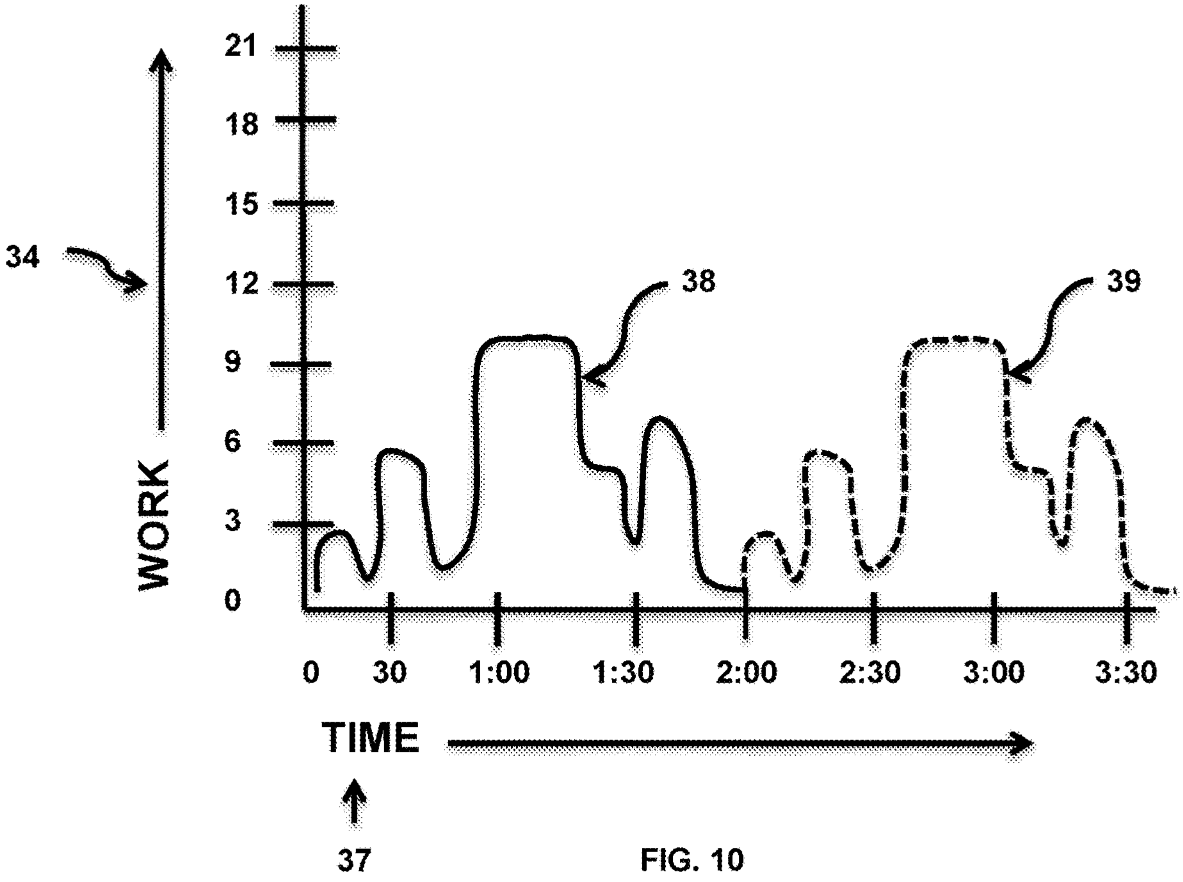
FIG. 10 is a graph showing a simple pseudo-random pattern of work/demand required by the system.

FIG. 10 shows one example of a pseudo-randomized pattern of work that can be delivered by the system 10. The work rate in METs is shown on the Y axis 34 and the time/duration of the test is shown on the X axis 37. In this example the pattern 38 repeats 39 after every 2 minutes, and requires approximately 1-2 changes in work every 30 seconds. Although the pattern is repeated it is complex enough that the subject is not likely to recognize the pattern. Work is at no more than 9 METs.

Figure 11:
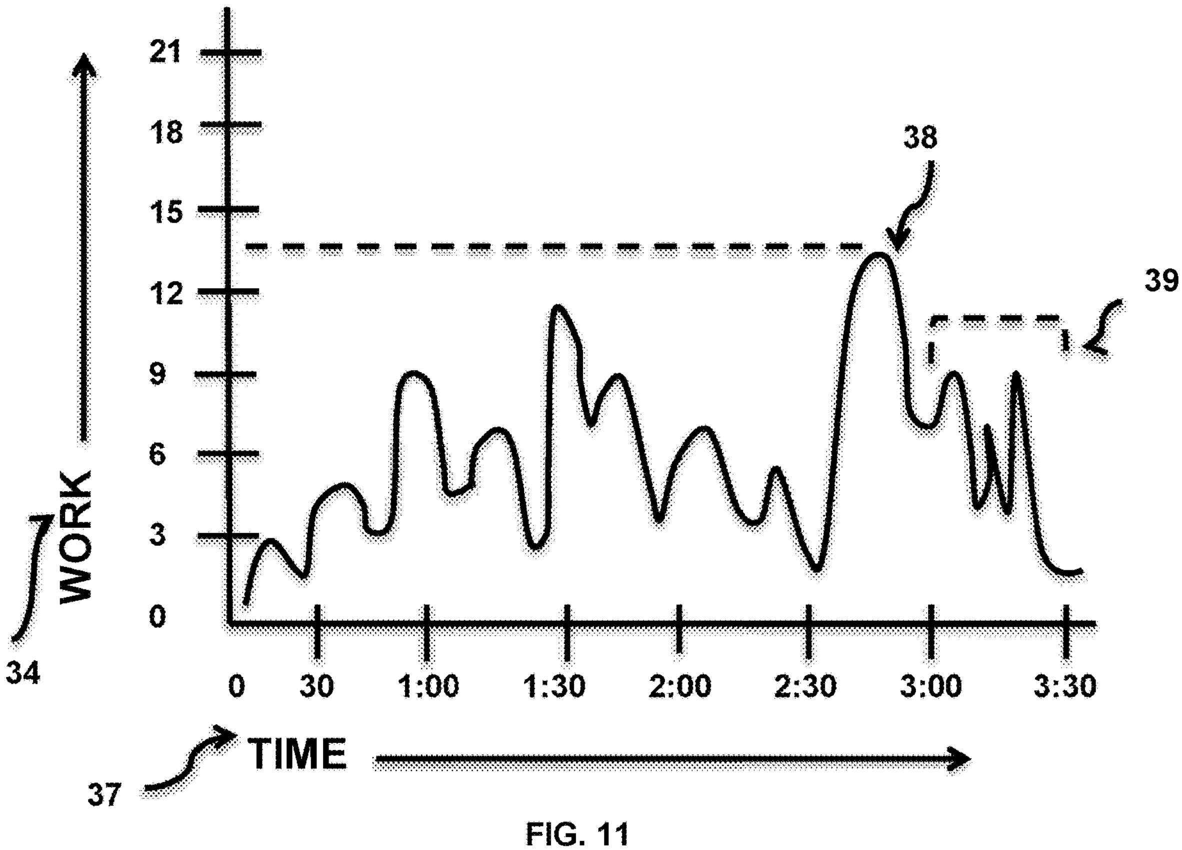
FIG. 11 is a graph showing a more complex and physically demanding pseudo-random pattern of work/demand required by the system.

FIG. 11 shows a more complex example of a pseudo-randomized pattern of work that repeats every 3:30. In this example, there are up to 6 changes in direction 39 in a 30 second period, and the demand for work is up to 14 METs 38. This pattern represents a more challenging test for a conditioned athlete. In order to be able to compare the subject's performance data from time to time, it is important to deliver the same pattern of movement for each and every test. This approach may capture a more accurate picture of the subject's cognitive, vestibular and orthopedic health.

Figure 12:
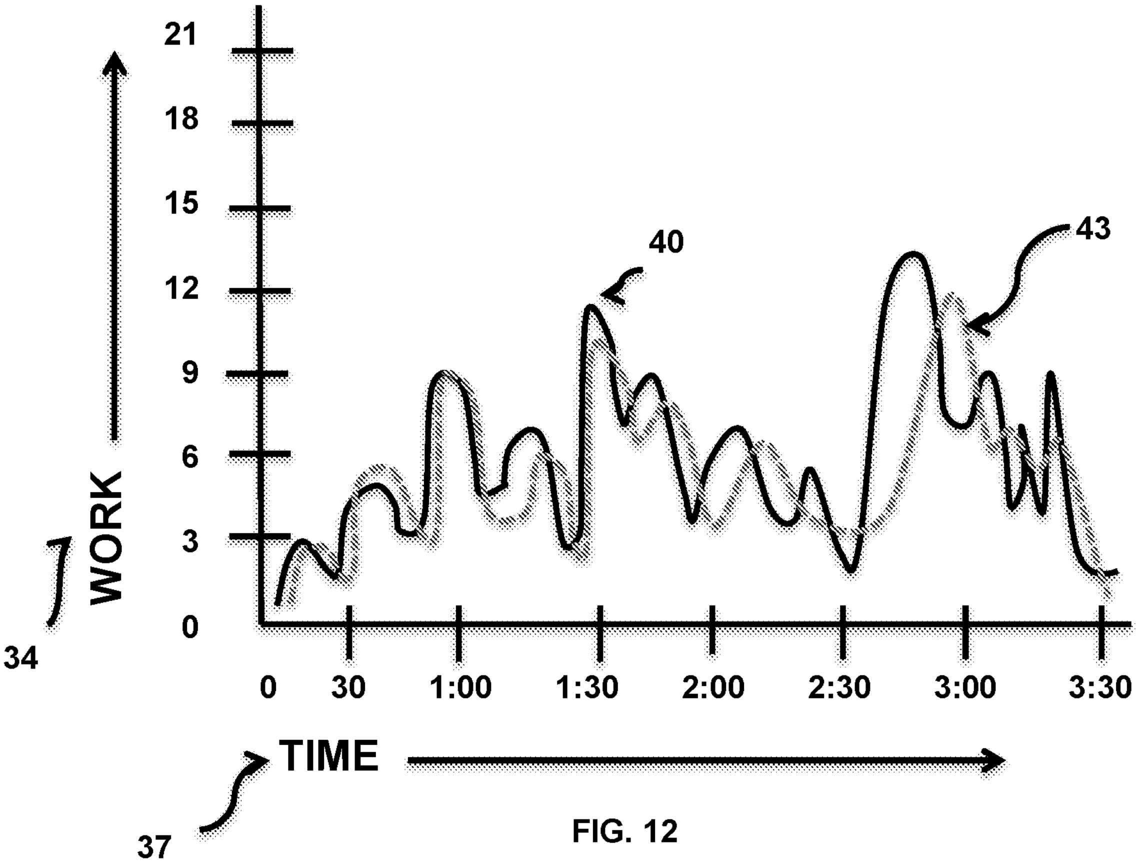
FIG. 12 is a graph showing the more complex and physically demanding pseudo-random pattern of work/demand illustrated in FIG. 11.

FIG. 12 shows a pseudo-randomized pattern of work in a solid black line 40, overlaid with the subject's pattern of work in a grey, dashed line 43. By overlaying the subject's pattern of work in this fashion, a visual picture can be derived of the percentage of compliance. The pattern shown is more complex and physically demanding pseudo-random pattern of work/demand illustrated in FIG. 11.

Triple-Task Paradigm

What is now described is a triple-task (TT) paradigm, a multi-task paradigm that adds a third task. In one embodiment the subject must perform three tasks simultaneously: interpreting information, a cognitive task; moving (translating) to unpredictable (to the subject) varying locations at an unpredictable (to the subject) varying movement rates or intensities (work rates); and having to make the movements using a shuffle step or push step, where translational movements (including lateral left-and-right movements) are accomplished without one leg crossing over the other. The three tasks act synergistically to challenge both the subject's cognitive reserves and physical performance capacities.

The movements may involve whole-body translations of varying length and/or direction, to varying locations. The variations may appear random to the user. The length of the individual translations may be no greater than 30 feet or no greater than 50 feet, to give a pair of non-limiting example lengths, with the recognition that a wide variety of other lengths for the translations are possible. As another non-limiting example, the transitions may have an average length of about 5 feet, for example an average length of from 3 feet to 7 feet.

The testing may occur over any of a wide variety of lengths of times. For example, the testing may take 1 to 20 minutes, 30 minutes, 40 minutes, or 50 minutes or longer, to give a few non-limiting example of possible test durations.

The interpretation of information may include interpreting symbolic visual information, such as a meter or alphanumeric display instructing the subject as to the movement rate to be achieved during the testing. The display may communicate the work rate of the subject (and the target work rate, and/or the difference between the actual work rate and the target work rate), in both analog and digital representations, as described above with regard to the DT paradigm. Alternatively either the analog or digital representations may be used. As noted above this movement rate (work rate) varies during the testing in a way that appears random and unpredictable to the user, increasing and decreasing at intervals of time. The instructed rate of movement (work rate) may vary over relatively small time intervals, for example less than a minute, and perhaps with some time intervals from two or three seconds to 8-10 seconds, to give some non-limiting example values, with the recognition that a wide variety of other time intervals may be used as alternatives. Other time intervals for the movement rates may be used instead. This allows measurement of explosive (high work rate) movements of several seconds, multiple times during a single test session. The need to interpret (or process) information on a continuous (or nearly continuous) basis provides a neurological load on the subject during the other tasks.

The full-body movement to seemingly random (unpredictable) locations, with unpredictable changes in rate, provides a physical challenge to the subject, which challenge may correspond in at least a physical task, such as a sports-related task. The task involves bouts of slower movement interspersed with bouts of faster (explosive) movement. One goal of a MT paradigm may be to obtain data for a large number of explosive movements in a single test, for example 5-10 (or more) explosive movements, although any of a wide variety of other numbers of explosive movements may be utilized. The subject must respond to instructions on where to move and at what work rate to move. The instructions may be delivered using a display device, such as described above in relation to various embodiments of the DT paradigm. The display may show a virtual representation corresponding to the physical space in which the subject moves. In the virtual space there may be some sort of symbol at a location in the virtual space corresponding to the subject's location in the physical space. There may also be a target indicating a goal of where the subject is to move at any given time, for example by making a full-body movement within the physical so as to cause in the virtual (displayed) space the symbol indicating the subject to intersect with the displayed target. At that point a new target may be displayed to the subject, at a new location within the virtual space corresponding to a new location within the physical space to which the subject is to move next. The magnitude and direction of the full-body movements that the subject is directed to successively undergo may appear random (or unpredictable) to the subject, varying without apparent pattern (the variation may be patternless, or part of pattern that not easily determinable by the subject).

The maintenance of movement rate may involve attending to and interpreting displayed movement rate information. The information may be communicated in a symbolic display, such as by use of a meter, and/or may be communicated by numbers and/or letters. Noncompliance with the instructed movement rate, such as a deviation by a predetermined amount or percentage from the target movement rate, may be communicated in any of a variety of suitable ways, such as by activation of one or more colors indicating a work rate that is too high or too low, or by other visual indicators, such as a flashing display portion or indicator.

The enforcement of kinematic form, for the example the enforced shuffle step, is a physical task that must be maintained by conscious will. The shuffle-step may also described as a push step, where the subject pushes off a back leg (furthest from target location, the end location of the present full-body translation) and stepping with front leg (nearest to target location). The system may involve tracking a number of different points on the body of the subject, for example tracking 30 or more points on the subject's body. The points tracked may include multiple points on each of the limbs, as well as points on the trunk and head. By tracking movement of the legs the desired kinematic form of movement may be enforced. For example a deviation from shuffle-step movement can be determined by tracking points on the lower legs (e.g., at feet or ankles) and those on the thighs (or the trunk). When the relative location of left/right points on the lower legs is the opposite of those on the thighs or trunk, this is an indication that the subject has crossed his or her legs (making a cross-over step), violating the shuffle-step kinematic form. The ability to track each leg individually and accurately may also be enhanced by enforcing a shuffle step, while allowing the subject to execute either a crossover step or a running-like movement to reach the next designated virtual target introduces material measurement variability/inconsistencies. The contributions of each individual limb would be unknowable, thus precluding the reliable assessment of moment to moment performance of each individual leg. The violation of form may be communicated to the subject, for example by a visual indication on the display screen or an auditory indication. The system may ignore or omit from calculations or analysis movement segments for which a cross-over step was detected.

The shuffle-step kinematic movement form may aid in making determinations of subject performance in an ordered way, enabling for example better comparisons of performance done in different tests at different times. For example reaction time might be measured for movement of the front leg (the leg closer to the target of the translation movement in question), but acceleration and velocity might be determined using measurements of the back leg (the leg farther from the target). Comparison of tests done at different times may allow comparison of baseline (e.g., pre-injury) tests with tests done after an injury, such as in various stages of recovery.

The TT paradigm (TTP) acts to repeatedly and frequently increase lower extremity physical stress levels to improve the detection of movement deficits directly relating to the subject's health and conditioning. The TT paradigm thus may be used to detect previously undetectable movement asymmetries and performance deficits for situation that range from return to physical activities post a lower extremity orthopedic (such as a knee or ankle) injury, a neurological injury (such as a concussion), or for assessing the risk for falling/mobility in aging populations. It is particularly well suited for the detection of heightened risk of orthopedic injury in healthy populations, as well for the management of exercise and rehab programs.

The synergism of the multiple tasks markedly improves measurement sensitivity and accuracy by providing greater fidelity with the cognitive and physical challenges of dynamic, real world environments. The result is an evaluation that more fully challenges the subject's cognitive prowess (reserves) and physical movement capabilities. This can more accurately assess the integrity of the subject's lower extremities (i.e. knees and ankles) and lower back, while the subject's cognitive resources are concurrently challenged. The subject's performance data obtained during such high physical and cognitive stressful movement scenarios is more revealing of asymmetrical movement patterns resulting from lingering injury, insufficient recovery, training effect, and other conditions.

The TT paradigm may include many features, for example: 1) ensure compliance with the movement protocol; 2) measure the fundamental performance components of movement, i.e. reaction time, acceleration, deceleration, velocity for each moment segment; 3) deliver spontaneous visual cues, which is requisite to measuring reaction time and other components of reaction-based sports; and 4) to accurately quantify the depth of the subject's stance, i.e. the location of the subject's "center of gravity."

In sharp contrast to tests of isolated capacities, the TT paradigm is specifically configured to more fully challenge the subject's sensory, cognitive and neuromuscular systems than other known systems. During the development phase of the TT paradigm, the individual contribution(s) of each task was/were observed/characterized. It was determined that the concurrent (collective) contributions of the three tasks strongly suggested a potent synergism was achieved. This synergism proved especially critical/relevant for populations with high performance capabilities, such as athletic populations. For such populations, assessments providing insufficient challenges/imposed stress would be insufficiently sensitive to elicit/detect "faults" (deficits). Faults may present in a number of ways including as reduced levels of compliance when responding to the prompted direction and speed of movement (determined by reaction time, decision-making, acceleration, velocity, etc.), early fatigue attributed to emotional stress, breakdown of form (kinematics), insufficient cardiorespiratory conditioning, exaggerated heart rate at a given work load, etc. It has been observed that the synergies created by the concurrent delivery of three distinct tasks elicited a greater number of uncoordinated movement responses, exaggerated heart rates at a given work rate, slower reaction times, hesitation, etc. It is believed that elimination/deletion of any one of the three tasks would act to reduce or even eliminate the faults observed, thereby reducing the efficacy/sensitivity of the assessment.

Mental faculties may have critical roles in maintaining overall situational awareness by redirecting attention to important environmental cues and simultaneously choosing the appropriate anticipatory motor program necessary for coordinated movements. Visual-spatial disorientation may lead to task uncertainty, attenuated muscle activity, and poor coordination. Similarly, if an athlete is attempting to mentally negotiate multiple sensory stimuli or motor tasks simultaneously, the additional cognitive load may be enough to slow reaction times and processing speed and to diminish knee-stiffness-regulation strategies. All of these factors may play into injuries and injury avoidance, and therefore may be considerations when determining whether a subject is fit to engage in an activity that could cause injury. In the TT paradigm, two speedometers (one digital; one analog) may act to continuously redirect (distract) the subject's attention; to create visual-spatial disorientation. Compliance with the TT protocol necessitates that the subject constantly divert her attention from the targets (destination) to the ever changing movement rate meters, all while maintaining the prescribed movement strategy. Plus the subject must correctly interpret and act on this symbolic info.

The TT paradigm may provide advantages relative to a system in which the subjects avatar interacts with a virtual opponent that is also displayed, and that the subject either needs to mimic motions of (follow) or evade. By way of example, an assessment that may be structured as a game simulation employing a virtual opponent that the subject's avatar interacts with. In this example, the virtual opponent may attempt to follow or evade so as to prompt the desired movements from the subject. Though such an interaction of value in certain applications, the (relatively limited) cognitive demands (cognitive overload) of this approach is analogous to a driver on a highway "mindlessly"/reflexively following the car in front. It is a task that requires relatively little concentration and cognitive processing, as the driver can rely on the lead car to determine and maintain the desired speed and direction. This approach limits the subjects' focus solely on a single object, i.e. on the car ahead. The driver doesn't have to independently process analog and/or digital visual information, such as may be displayed on the car's speedometer, or Google Maps to navigate his route. It is important to note that this relatively low level of processing demands (cognitive reserves) may be particularly evident with experienced (accomplished) athletes. Athletes train innumerable hours to learn to reflexively respond in an offensive or defensive role.

By contrast, the TT paradigm removes the subject from this "instinctive" "follow the leader" role (for example, a basketball player in a defensive role) to one where the subject must continually scan large portions of the displayed virtual world to obtain and process constantly changing symbolic visual information regarding the prescribed movement rate, all the while simultaneously locating and moving to intercept the correct visually-determined target/destination. In addition to complying with the imposed ("isolated limb") movement strategy. In some embodiments of the TT paradigm, the subject must move her avatar to "intersect" with the (continually) displayed virtual target while concurrently diverting her visual attention from the displayed targets to the analog and digital speed meters and then back again to the virtual targets. These concurrent and divergent sensory and cognitive tasks challenge the subject to process and retain this visual analog and digital information, which than has to be correctly act upon.

Measured performance parameters can be compared to a previous baseline tests and/or other prior subject assessment (s), or to established normative data. The degree the subject remains in compliance with TT paradigm or protocol may be compared to a measure of "perfect" compliance, such as a score representing the difference over time between the subject's actual degree of compliance and a perfect degree of compliance. The subject's score could also be compared to previously collected normative data and/or previous tests by the subject. Compliance factors include movement rate, correct performance of the movement strategy, etc.

For example, a healthy athlete may be in compliance for 78% of time compared with 47% of the assessment time when the athlete is in a state of Overtraining, exhibiting signs of an orthopedic or neurological injury or numerous other undesirable presentations/conditions. This data could be presented in a graphical format with Time along the X axis and Percent Compliance along the Y axis. One plot (line) could represent perfect compliance and a second line could represent the subject's actual (measured) compliance. The difference between these lines may illustrate/document the degree of non-compliance with the assessment protocol. Also calculated and presented may be a comparison between the subject's time in compliance at various prescribed movement rates/speeds. For example, it may illustrate/depict that the subject was in compliance 67% of the time at slower movement speeds in contrast to 39% of the time at higher movement speeds. Movement performance data/metrics for each movement direction may be reported for as few as two and perhaps as many as 8 or more vector directions.

To characterize "kinetic" (movement) health, TTP measures and reports performance metrics such as moment-to-moment reaction time, acceleration, velocity, deceleration and distance traveled in each movement vectors. Physiological measures such as heart rate and calculated work rate provide relevant data regarding the subject's work rate during the entirety of the test. If, for example, the subject's heart rate at a given work rate is exaggerated or blunted, it may be clearly evident.

The subject's reaction time may be reported in hundredths of a second. Reaction time maybe averaged for 30 second time periods and displayed vs time to illustrate the effects of work load on this parameter. This is only a non-limiting example, and it will be appreciated that many other suitable time periods for averaging may be used as alternatives. Reaction time provides valuable insights regarding any degradation of attention span, which is cited, for example, as a key indicator of a subject's propensity to fall in geriatric populations. The report of reaction time may be done for different movement directions, and/or for different legs used by the subject to initiate movement.

Aligning these performance values alongside the METS vs. time curve allows determination of the effects of progressive and variable work on the subject's ability to react and move.

FIGS. 13 and 14 show an example assessment result for a user, showing results for baseline and current tests for a number of measures. FIG. 13 shows a summary of results on balance, and scores involving maximum exercise level (METs) achieved, total distance moved, time of the test, average and maximum heart rate, average and maximum speed, and average and maximum jump height. All of these are compared with baseline values. The general comparison shown in FIG. 13 shows a significant deficit in the user tested, with the user's current test results showing a significantly elevated heart rate at a lower exercise level.

FIGS. 14A and 14B show the results in eight vectors (forward, forward right, right backward right, backward, backward left, and forward left) for four measured parameters, reaction time, speed, acceleration, and deceleration. The results for each measure are supplemented by an overall left/right difference in performance. Again the results for current testing are compared to those from baseline testing. The results for all these measures can yield a variety of information regarding the user. For example, in the specific results shown in FIGS. 14A and 14B there is a general deficit in leftward acceleration and deceleration of the user, which may indicate an injury to the left leg (knee, hip, ankle, or foot) of the user.

This vector analysis is obtained simultaneously with testing of the subject's cardio-respiratory fitness, through the tracking and measurement of the subject's movement in multiple vectors. This provides a quick, objective, and accurate assessment that introduces interactivity and provides previously immeasurable metrics. This is in contrast to what is provided by conventional speed, agility, and quickness drills that are limited to only measuring elapsed time to complete a pre-planned course.

The graded testing may start from the user standing at rest, and begin with the exercise intensity at 1 MET, with testing and varying intensities continuing until such time that the user elects to quit due to fatigue, i.e. achieves their "volitional maximum." Depending on the user, ranging from "at risk" populations (able to use the system with medical clearance) to elite athletes, tests can be terminated based on several factors that include: volitional exhaustion; a predetermined percentage of maximum heart rate, such as 60%-85% of the user's predicted maximum for their age; a predetermined percentage of degradation of physical performance (such as movement rate); or the manifestation of certain predetermined symptoms, such as symptoms of distress.

The subject's heart rate may be continuously monitored via telemetry. Reaction time, acceleration, velocity, deceleration, and distance traveled may be continuously measured and reported by movement-direction. test protocols. The graded testing involves progressively increases physiological demand on the subject. During the early stages of the test, demands are limited on the subject, and are progressed to intensities appropriate for the subject. In some populations cleared for strenuous exercise by a physician, a "maximal effort" improves the accuracy and reliability of the test protocol.

As described earlier, METs ("metabolic equivalent") is a measure of exercise intensity based on oxygen consumption. One MET may be defined as the amount of oxygen a subject consumes (or the energy expended) per unit of body weight during 1 minute of rest. It is equal to approx. 3.5 milliliters (ml) of oxygen consumption per kilogram (kg) of body weight per minute, or 1 kilocalorie (kcal) per kg of body weight per hour. Work Rate may be expressed in Watts, as is supported by an abundance of quality normative data developed for use with clinical cardiac exercise tests. Reaction time may be reported in hundredths of a second.

The system may measures the elapsed time from the presentation of the visual cue until the initial movement in the correct direction. Time may be averaged for 30 second time periods (or other suitable time periods), and may be displayed vs time. Aligning these values alongside the METs vs. time curve allows one to determine the effects of progressive work efforts on the subject's ability to react.

Acceleration may also be averaged for 30-second time periods (or other suitable time periods), and may be displayed vs. time. Aligning acceleration vs. time and the METs vs. time curves allows one to determine the effects of progressive work efforts on the subject's ability to react and to accelerate. These timelines optionally may include other parameters measured by the system, such as reaction time, deceleration, and speed.

TTP elicits subject responses to cognitive challenges at varying metabolic (work) rates (these prompted work rates are typically unpredictable to the subject) to objectively document increasing physical stress on cognition (as measured by reaction time and movement accuracy/compliance) and well as the resulting effects on the subject's accelerations, movement speed, decelerations in a variety of movement vectors that may range from as few as two to as many as eight movement vectors or more.

With regard to preventing overtraining, characterizing whole body recovery/response to exercise provides previously unavailable critical data to more effectively manage the stress-regeneration cycle as well as detect heightened risk for orthopedic or brain injury. For example, the diminishment of reaction times and accelerations, as well as an exaggerated heart rate for a given work load compared with baseline tests may expose (detect) early fundamental signs of increased risk of overtraining.

TTP's imposed movement strategy contributes to more sensitive, accurate and repeatable metrics relating to gait termination. Gait termination (GT) may be assessed by measuring the deceleration ("braking") generated by the leg intercepting/satisfying a movement cue. GT metrics depends on accurate knowledge of the actions of the braking limb, and enforcing the TTP movement strategy discussed above ensures this happens. It has been observed in the past that altered propulsive and braking forces may persist despite a subject achieving baseline values on standard concussion clinical tests. GT testing can detect both acute and lingering motor control strategy alterations following concussion. GT thus may be more sensitive measurement than widely used tests such as a visually scored BESS test. Impairments in balance persist longer than indicated by clinical tests. Examining GT in the context of TTP may aid in evaluating these impairments, allowing identification of acute and lingering motor control strategy alterations in post-concussion subjects. Determination of such strategy alterations may be seen as a barrier to a subject (such as an athlete) resuming full engagement in taxing activities (such as sports). Traditional concussion assessments may not identify such impairments.

In executing the TT paradigm, a system similar to the system 10 (FIG. 1) may be employed. One example of a suitable camera or sensor for tracking a subject is the KINNECT system marketed by Microsoft, although any of a variety of other cameras/sensors may be used to track movement of the subject, or parts of the body of a subject.

The TT paradigm evaluation/testing may be performed on a system similar to that used for the DT paradigm evaluation/testing, such as the system 10 (FIG. 1) that is described above. The hardware requirements for the technology may be centered around a motion-sensing camera system capable of capturing human movement. A camera being used for the purposes of building this application herein may have at least 10 frame per second or greater capture rate. Within the frames of data being captured data the physical position of various limbs of the participating user in a 3-dimensional plane may be used for the calculations being performed. A camera such as the KINECT version 2 camera by Microsoft is an example of a suitable camera that provides the desired output, a good capture rate, and 25 joint positions of the participating user which can be used to calculate limb locations. Other cameras while providing similar functionality may capture data other than specific joint positions that can be used to provide the data for the required calculations.

In order to utilize the camera system a person computer will need to be constructed meeting the specification of the camera system. For example, in the case of the KINECT v2 camera this is a computer running a 64-bit, dual core processor with at least 4 GB of RAM, a USB 3.0 port and a graphics card that supports the DirectX 11 libraries. Other cameras and even future versions of the Kinect camera system may modify these requirements to their needs and specifications.

In the operation of the computer system and the application being designed it is also important to obtain a viewing monitor. This can be a TV screen or computer monitor that supports a resolution providing the desired view of the operating environment. A recommended resolution of at least 1920×1080 is sufficient, although it will be appreciated that this is not a strict requirement. Lower resolution may also provide adequate viewing of the system but it is important to ensure no part of the screen is being cut off for the user's viewing experience.

Additional peripherals for the personal computer may include a working keyboard and mouse.

The software behind the application described herein can be written by someone of ordinary skill in the art. There are many ways the actual viewing application can be configured and laid out. The software application itself can be written in any suitable language that provides support or a means for capturing the data from the camera system. While a camera system may provide an Application Programming Interface to assist the developer with the programming interface between the software and the camera system, it is also likely that other libraries or tools may be able to provide the data in a larger breath of programming languages. Upon developing the core component of the data acquisition of the movement of the individual from the camera system, the storage, calculations, and any additional work of the designed application can be done in any technology supporting said functionality. This application does not rely on a specific technology, database software or stored media to perform the desired calculations and storage of the data. Thus technologies and languages may be as consistent as the developing programmer wishes.

The software application itself can be housed within a desktop application or any application where the software can interact with a locally connected camera system. While there are methods to perform, the camera capture remotely using Wifi or Bluetooth technologies the ideal setup is for the camera to be directly connected to the computer running the application. This will result in the best performance and responsiveness of the application. However these attributes are only example attributes for the software.

The software application preferably has a visual component allow the user to see a representation of their movements on the screen. An example of this movement would be to display an avatar representing the user on the screen. As the user moves within the field of play, the avatar mirrors that movement in the same direction as the user. The surrounding environment of the application can be anything from a realistic view of a gymnasium or performance studio, to an outdoors, to just anything imaginable. The main focus is the user's ability to see the movement they are making represented on the screen.

The visual display also includes presentation of stimuli that to which the user responds. The stimulus of the game (or evaluation) is that in which the user is shown an object or figure on screen with the instruction to move to that object's location. Once the object's location is reached another object is displayed in another location and the movement of the user continues. Placement of the next stimuli should be on a random basis such that the user is not able to anticipate the next object. This movement and stimuli pattern can continue until the parameters of the exercise are complete. The parameter for completion is not specific to the evaluation here and may be a set number of targets or a time range. The user could also be stopped for poor performance during the application. Such poor performance would be characterized as moving in a non-preferred manner, moving too slowly, movement in the wrong direction or failure to move at including leaving the playing field and remaining off screen.

In the logic of the application the user being presented the stimuli will be tracked within the software based on their movement. Their movement will be tracked for analytical purposes of the speed, reaction time, acceleration and deceleration of the user's movement.

In addition to the various elements described above in connection with the system 10 (FIG. 1), the TT paradigm may show on the display 26 (FIG. 1) some sort of indication when the subject 42 (FIG. 1) is out of compliance with the required kinematic movement form, such as the shuffle-step movement described above.

As discussed earlier, many measures of the subject's movement may be captured during testing, with at least some of those measures used to characterize the subject fitness for performing tasks. For example data may be gathered on moment-to-moment reaction time, acceleration, speed, deceleration, and distance traveled in each movement vector. A subject's fitness for performance in a task, such as being able to return to play in a sport, may be evaluated based on this data, alone or in conjunction with data gathered in earlier tests. Such earlier tests may include baseline tests or pre-injury tests, and/or post-injury (or post-event) tests at earlier points during recovery.

The data evaluation may include comparing results for different vectors of movement with one another, and may also involve comparing such a comparison to a prior comparison, for instance performed using baseline data. For example a new test may show that a subject has a reaction time difference of 20% between movements to the right and movements to the left, a difference that was not present during baseline testing. This may be used as an indicator of continued physical injury, and perhaps incomplete full return of cognitive functioning. The characterization of the subject's condition may be made in any of a variety of ways, including in a binary fashion (e.g., cleared for resumption of activities vs. not cleared), in a quantitative fashion (such as by a numerical score indicating some sort of fitness), or in a qualitative fashion, (e.g., the subject has moderate asymmetry in her deceleration).

FIG. 15 shows a table of example normative ranges for data that the system reports, with ranges for "excellent," "good," and "average" performance for each measure. These ranges are only examples, and other characterizations of performance are possible. Nonetheless, evaluation of a subject's condition may involve examination of the number of parameters for which the subject's performance has degraded one or more categories, relative to baseline results. Being cleared for resumption of full activities may involve return of all parameters to the same category that they were in in baseline testing, to give one non-limiting example.

Figure 16:
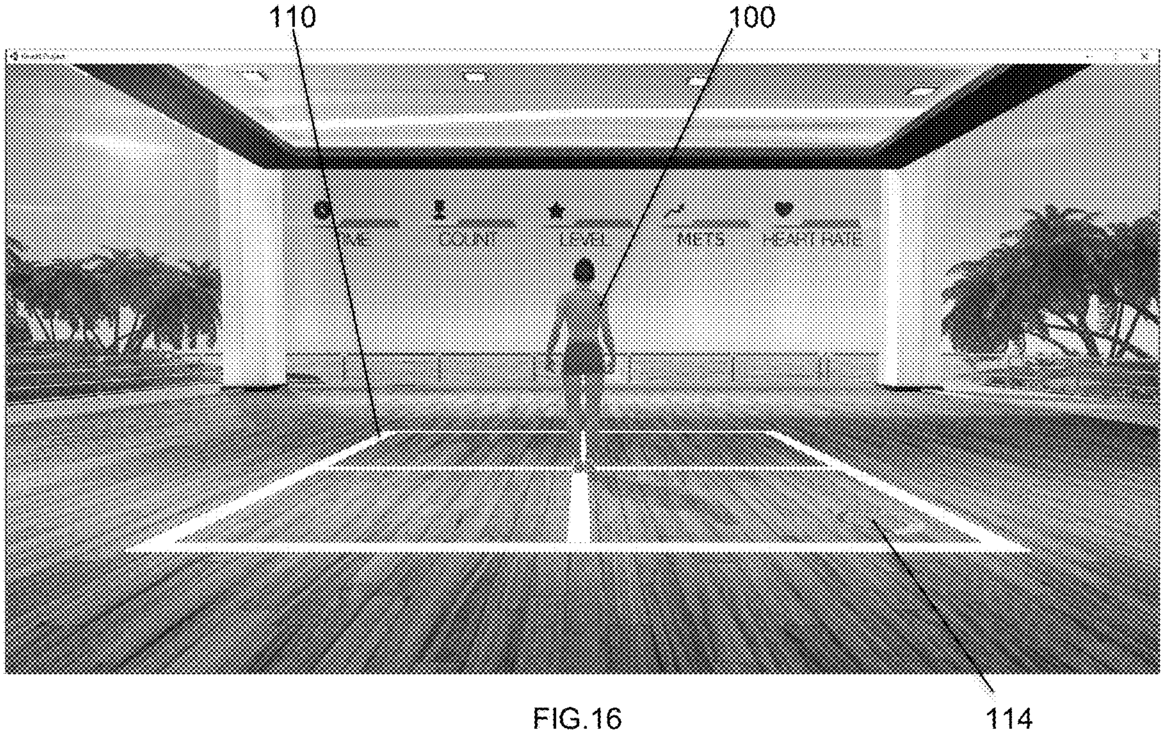
FIG. 16 is a screenshot illustrating an initial calibration of the system before beginning of a test.

FIGS. 16-20 as screenshots illustrating various aspects of testing using the protocols described herein. FIG. 16 shows a situation where the subject (represented by the icon 100) is located in the center of a field or area 110 in which the testing is to occur. This is done for purposes of calibration. After the calibration process is completed, the subject is directed to a start position target 114, a location where the subject move for the start of testing.

Figure 17:
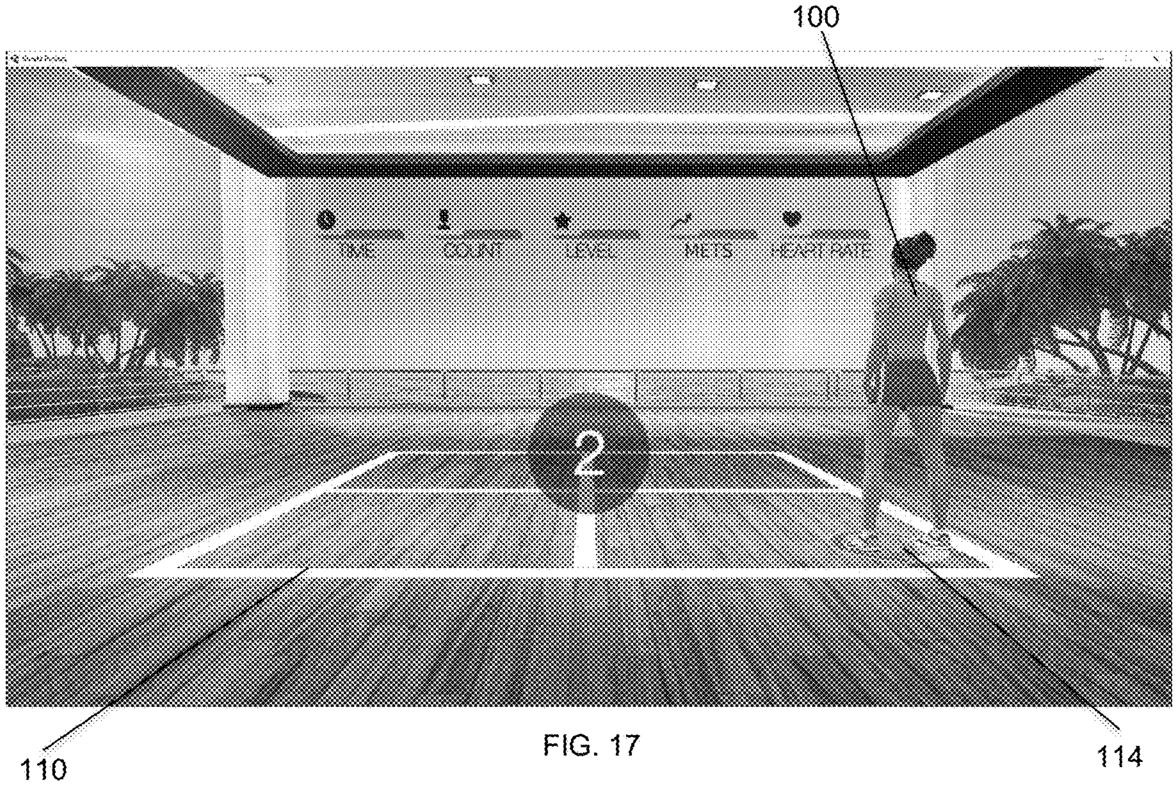
FIG. 17 is a screenshot illustrating a countdown to a first movement cue.

Once the subject moves to the start position target 114, the subject stands still during a countdown, waiting for the first movement cue. This countdown is illustrated in FIG. 17.

Figure 18:
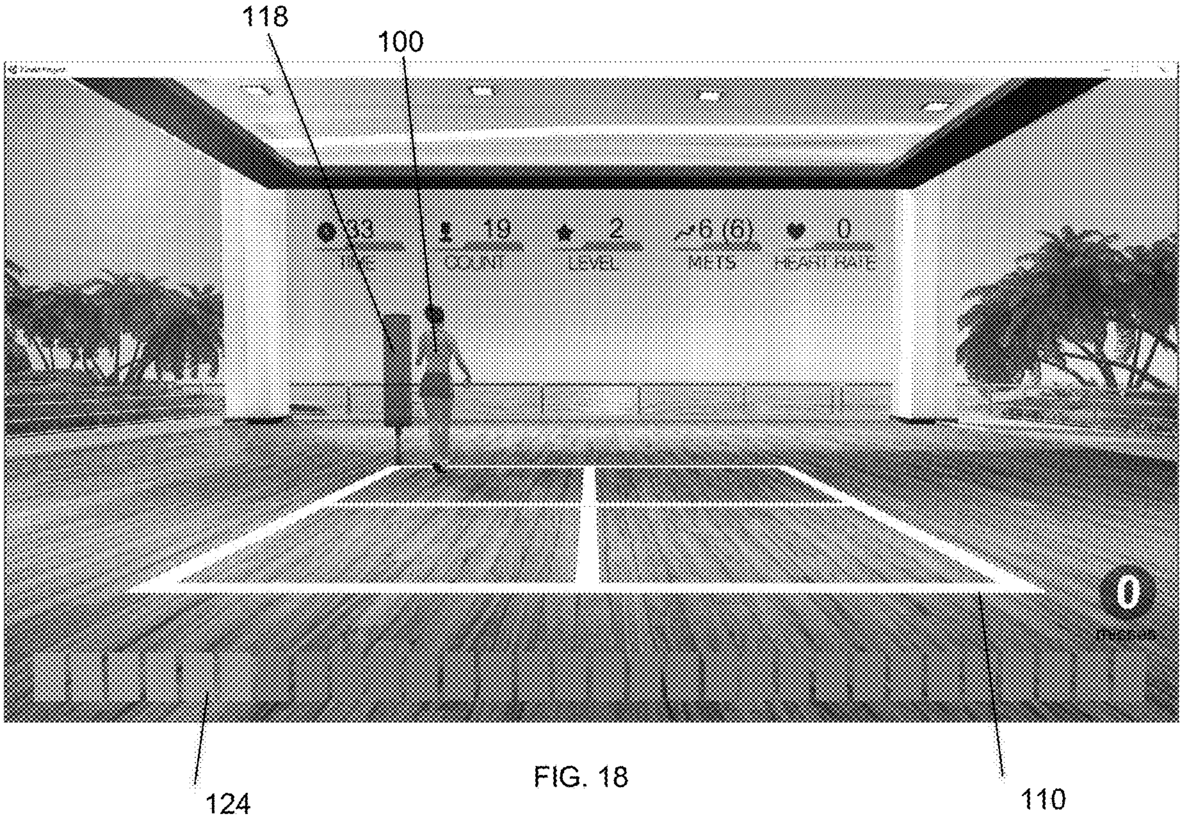
FIG. 18 is a screenshot illustrating movement in response to the first movement cue.

FIG. 18 shows the subject responding to a cue (a bumper icon 118) in a northwest corner of the field or area 110. Pace is controlled by a communicated demand for either METs or speed (for example in feet per second). The required pace (6 METs in the example) is shown in parentheses at the top of the screen in an analog meter 122. The actual pace of the participant or subject appears in real time to the left of the parentheses in the analog meter 122, as well as in a digital meter 124 at the bottom of the screen. A green indicator on the digital meter 124 indicates compliance, while blue indicates that the subject is moving too slowly, and red indicates that the subject is moving too fast.

Figure 19:
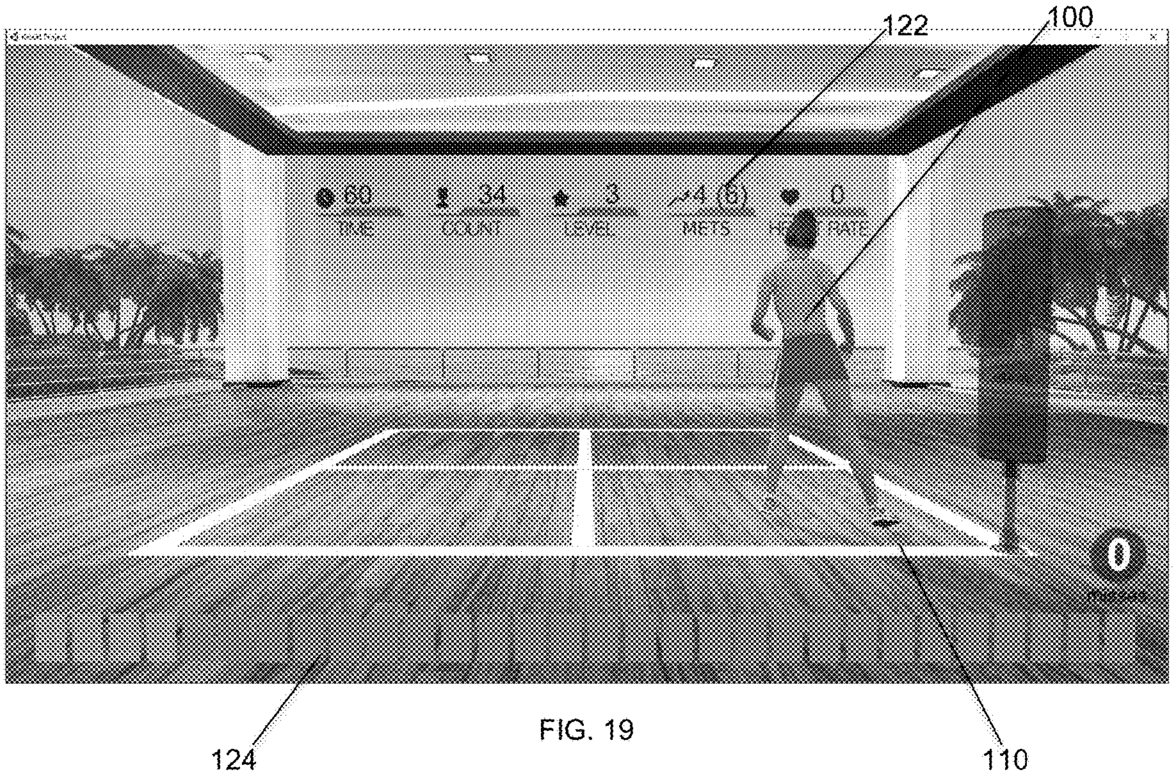
FIG. 19 is a screenshot illustrating movement in response to a second movement cue.

FIG. 19 shows the subject responding to another cue, this one in the southeast corner of the field 110. The pace prescribed by the system as illustrated in FIG. 19 remains 6 METs. However the subject is traveling at only 4 METs as illustrated in FIG. 19, which is reflected both in the analog meter 122, and in the blue color in the digital meter 124 at the bottom of the screen.

Figure 20:
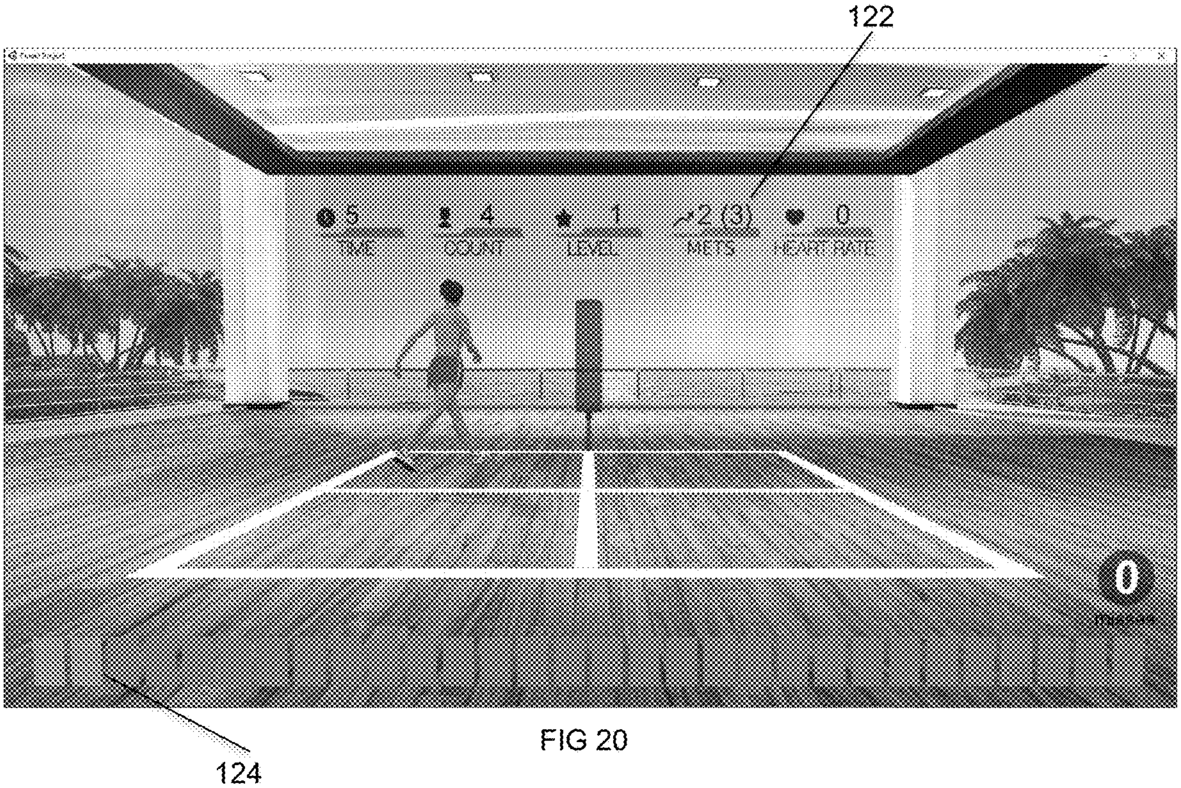
FIG. 20 is a screenshot illustrating movement in response to a second movement cue, at a reduced movement pace.

FIG. 20 shows the situation where the pace demand has dropped from the 6 METs of FIGS. 18 and 19, to 3 METs. The participant or subject dropped her pace too far and is not in compliance as shown by the blue bars in the digital meter 124 and by the numerical register "2(3)" in the analog meter 122.

Figure 21:
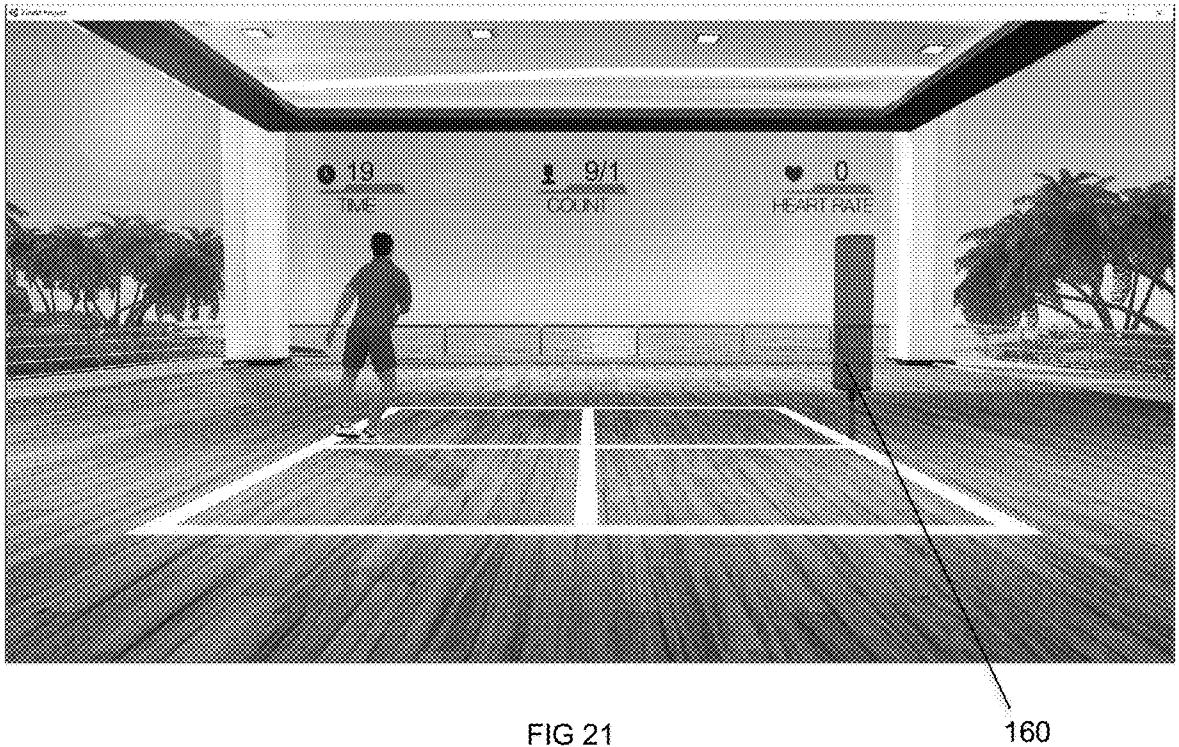
FIG. 21 is a screenshot illustrating a first part of a shuffle-step movement.
Figure 22:
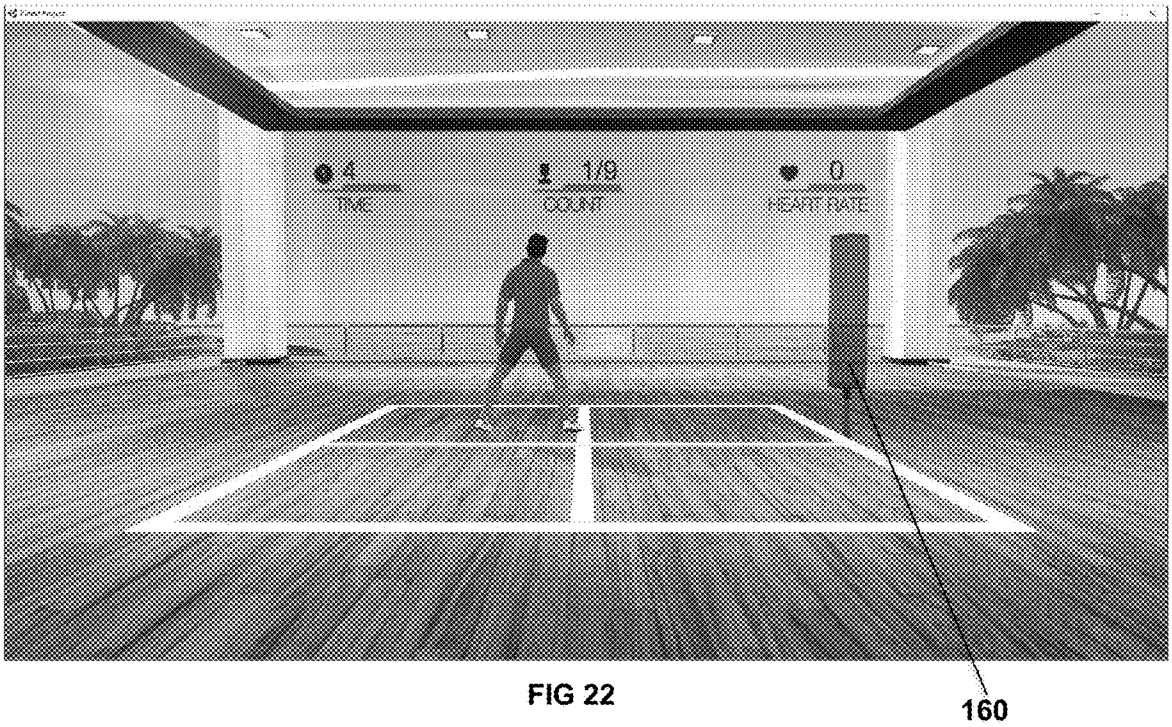
FIG. 22 is a screenshot illustrating a second part of the shuffle-step movement.
Figure 23:
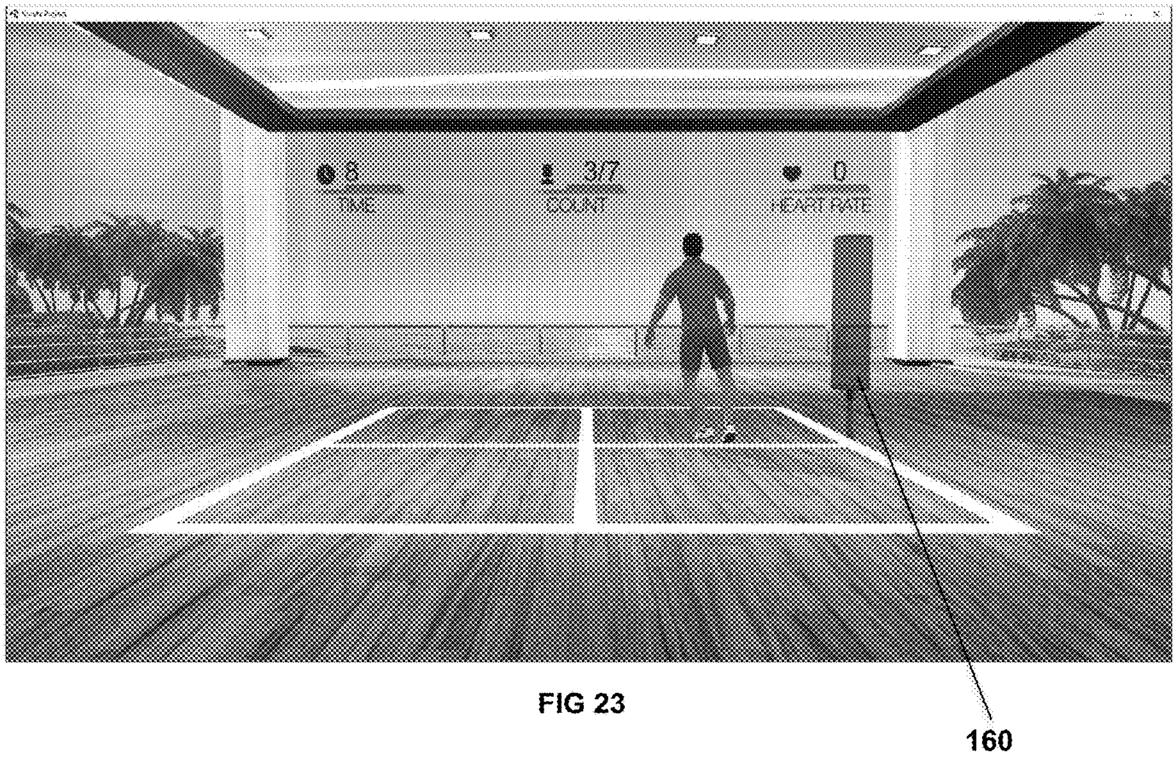
FIG. 23 is a screenshot illustrating a third part of the shuffle-step movement.

FIGS. 21-23 illustrate the shuffle-step gait compliance that may be enforced by the system. Pain from injury and/or weakness may lead to compensatory behaviors. For example an athlete striving to optimize his time to distance between targets may use a crossover step if his trained lateral shuffle is painful or slow due to injury. For lateral movements, the may enforce a shuffle step, which is illustrated in FIGS. 21-23 for successive position of the subject moving toward a target 160.

It also may be possible to measure stride length, alone or in conjunction with other parameters. Some of the material below is taken from the article "Gait Variability: Methods, Modeling and Meaning," by Jeffrey M. Housdorf, Journal of NeuroEngineering and Rehabilitation, 2:19 (2005). The Housdorf article provides information concerning the quantification of stride-to-stride fluctuations," and is incorporated herein by reference in its entirety.

As noted above, the TT paradigm described herein imposes novel cognitive and movement challenges while providing for the accurate movement tracking of a subject's legs in response to visual prompts in multiple vector directions. Such vector directions may include as many as 8 or more vectors. The subject movement performance may be preplanned or reaction-based, i.e. where the subject responds to unpredictable visual or auditory cueing.

In addition to the measurements of reaction time, the subject's stride length for each step undertaken in response to system cues may be measured. Additionally, the subject's reaction time associated with each step may also be measured. Temporal and spatial gait parameters may also include step width, step time and associated step length. Such measurements may be determined by the movement of the subject's foot, among other measurement points. Unlike in some prior art systems and approaches, the present approach (the MT approach described at length above) is a method of measuring weight-bearing performance via a DT or TT paradigm (more broadly, a MT paradigm) that acts to further challenge the subject's cognitive reserves. It is believed that these increased cognitive and movement challenges will result in a more sensitive and accurate characterization of subject status.

As noted by Hauser, "gait variability is a quantifiable feature of walking that is altered (both in terms of magnitude and dynamics) in clinically relevant syndromes, such as falling, frailty, and neuro-degenerative disease (e.g., Parkinson's and Alzheimer's disease)." In addition, "the nature of the relationships among the average gait speed, the average stride length, and the variability of these measures are critical to the study of fall risk. Although a reduced gait speed has often been viewed as a sign of fall risk, Maki showed that, at least among certain older adults, average gait speed and related measures are related to fear of falling, but not to the risk of falling per se, while measures of variability predict future falls." Further, "a number of other investigations demonstrated that the degree of variability may be more closely related to fall risk than average gait speed, average stride length, and average stride time. These results suggest that measures of gait variability may sometimes be more sensitive than other measures of gait, and that these measures may provide a clinical index of gait instability and fall risk." Also, "if one views gait variability as a reflection of the inconsistency in the central neuromuscular control system's ability to regulate gait and maintain a steady walking pattern, then it makes sense that measures of gait variability would be associated with instability and fall risk. A more variable gait in which the center of pressure moves over and beyond the base-of-support in a relatively uncontrolled, unstable fashion may predispose to unsteadiness and falls."

Studies have shown that variability was related to fall risk, but not to fear of falling. Indeed, studies of some types of dual tasking found that gait speed slowed when healthy subjects, young and old, performed a secondary dual task during walking, while the variability of stride and swing timing was unchanged. "In contrast, dual tasking not only reduced gait speed, it also increased variability among patients with impaired automaticity (e.g., Parkinson's disease patients). These findings are in line with the view that the regulation of variability is normally automated and requires minimal cognitive input."

Thus there appears to be merit in measuring/characterizing variability associated with a subject's stride length, in addition to stride width, step timing, and/or reaction time or any other related movement responses. Intraindividual Variability (IIV) refers to any variation in reaction times (RT) and/or stride length, in addition to stride width, step timing, and/or any other related performance responses for a given cognitive task. It is stated that larger IIV may reflect deficits of the frontal circuitry implicated in falls and gait impairment in geriatric populations. Across studies, IIV measures were consistently associated with falls in older persons and demonstrated some potential in relation to gait.

"Step length appears to be a strong discriminant gait parameter for elderly females highly concerned about falls: a cross-sectional observational study." In addition, "the review provided clear evidence that older adults exhibiting greater neurocognitive variability are more likely to experience a fall," and "this clearly suggests that in the present context, the IIV measures exhibited greater predictive utility than measures of mean performance obtained from the same task."

Also incorporated herein by reference in its entirety is a 2011 paper by Renata Noce Kirkwood et al., "Step length appears to be a strong discriminant gait parameter for elderly females highly concerned about falls: a cross-sectional observational study." Some relevant material from the Kirkwood paper includes: "High concern about falls is primarily associated with decreased step length. Step length could be used as a screening tool to identify elderly women with low and high concern about falls in order to target these groups in a rehabilitation programme aimed to slow reduction in gait velocity and mobility;" and "Individuals concerned about falls also adopt a more cautious gait, characterized by a reduction in velocity and step length . . . " Kirkwood observed that gait parameters appeared to most commonly collected "using a 5.6 m GAITRite instrumented walkway with embedded pressure sensors . . . . As the subject walks across the walkway, the pressure exerted by the feet on to the walkway activates the sensors, and the walkway senses the geometry of the feet and the relative arrangement between them in a two-dimensional plane."

Another example of a current system is LEGSys, a wireless wearable system for analyzing stride length, duration, speed and cadence.

Kirkwood reported that their "discriminant model revealed that step length had greater power to discriminate than either gait velocity or the Timed Up and Go test score. Gait velocity is directly proportional to step length in the gait cycle. A reduction in step length, and consequently stride, is one of the strategies used to reduce gait velocity. This reduction in step length has been observed in elderly individuals concerned about falls."

It has also been suggested that, " . . . under conditions of normal gait, the primary cause of a reduction in gait velocity among elderly individuals is physical limitation. It has recently been demonstrated in a group of elderly individuals (adjusting for age) that the factors most strongly associated with a reduction in gait velocity are reaction time and quadriceps muscle strength."

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method of evaluating a subject, the method comprising:

providing a display screen and a motion-sensing camera operatively coupled to a processor, the camera configured to detect a plurality of points along a body of the subject in three dimensions;

displaying, via the processor, a virtual environment on the display screen, the environment comprising a target for a shuffle-step movement, wherein the target is placed at locations determined by a pseudo-random algorithm executed by the processor;

prompting the subject, via the display screen, to perform a series of shuffle-step movements to the target, wherein the processor directs the subject to achieve varying target levels of movement intensity, and the target levels and durations are varied unpredictably;

tracking, in real time via the processor and camera, three-dimensional movement of the body;

detecting whether movement of the subject deviates from the shuffle-step movement by determining if one leg of the subject crosses in front of the other leg of the subject;

providing immediate feedback to the subject via the display screen when a deviation from the shuffle-step movement is detected;

calculating, via the processor, quantitative performance metrics derived from the tracked three dimensional body movement, including moment-to-moment reaction time, acceleration and deceleration;

calculating, via the processor, a work rate of the subject based on the tracked three dimensional body movement, including speed of movement and distance of positional changes;

determining cognitive function based on a comparison of reaction time to baseline data previously obtained from the subject at corresponding work rates;

displaying, via the processor, the calculated performance metrics and any statistically significant changes from baseline, wherein the metrics are reported in hundredths of a second and are not visually discernible without analysis by the processor;

displaying, via the processor, the work rate and a target work rate simultaneously; and enabling detection of subtle movement asymmetries or performance deficits, wherein the moment-to-moment reaction time is based on an elapsed time from presentation of the target on the display screen until initial movement of the subject in the direction of the target.

2. The method of claim 1, wherein the displaying the virtual environment comprises displaying the target in various locations in a representation of a physical area in which the subject moves.

3. The method of claim 2, further comprising displaying on the screen a virtual representation of the subject that moves within the representation of the physical area in response to movement by the subject.

4. The method of claim 3, wherein the movements of the subject are completed when the virtual representation of the subject intersects the target.

5. The method of claim 1, wherein all of the movements do not exceed 30 feet in length.

6. The method of claim 1, wherein the directing also includes varying duration of the varying target levels of movement intensity, such that both the target levels and the duration both vary during different series of the movements.

7. The method of claim 1, wherein the target levels of movement intensity are varied in durations of 10 seconds or less.

8. The method of claim 1, wherein the directing includes displaying a symbolic representation of the target levels of movement intensity, with the symbolic representation displayed on display screen that is visible to the subject during the shuffle-step movement.

9. The method of claim 8, wherein the prompting includes displaying on the screen a target that indicates where the subject is to move, wherein the target is moved on the screen from one location to another as each of the movements is completed.

10. The method of claim 8, further comprising providing notification to the subject when the subject deviates from the target intensity by more than a predetermined amount.

11. The method of claim 1, wherein the determining includes determining a measure of compliance of the subject with shuffle-step movements at target levels of intensity.

12. The method of claim 1, wherein data gathered during a translation in which the one leg of the subject crosses in front of the other leg of the subject, is not used in characterizing movement of the subject.

13. A method of evaluating a subject, the method comprising:

providing a display and a motion sensing camera operatively coupled to a processor, the camera configured to detect a plurality of points along a body of the subject in three dimensions;

displaying, via the processor, a virtual environment that includes an avatar and target on the display screen;

presenting on the display screen, via the processor, spontaneous visual cues to the subject by random placement of said target in the virtual environment to prompt said subject to perform shuffle step movements of varying speeds and movement vectors to the target, wherein the processor directs the subject to achieve varying target levels of movement intensity, wherein an avatar on the display is configured to replicate the movement of the subject;

prompting the subject, via the display screen, to perform a series of shuffle-step movements to the target, wherein the processor directs the subject to achieve varying target levels of movement intensity, and the target levels and durations are varied unpredictably;

tracking, in real time via the processor and camera, three-dimensional movement of the body;

calculating, via the processor, quantitative performance metrics derived from the tracked three dimensional body movement comprising a moment-to-moment reaction time, acceleration, speed, deceleration, and distance traveled for each movement vector of said subject;

calculating, via the processor, a work rate of the subject based on the tracked three dimensional body movement, including speed of movement and distance of positional changes;

comparing a degree of movement compliance of said subject to data reflective of a previously administered assessment of the subject via the processor;

determining cognitive function based on a comparison of reaction time to baseline data previously obtained from the subject at corresponding work rates; and enabling detection of subtle movement asymmetries or performance deficits, wherein the moment-to-moment reaction time is based on an elapsed time from presentation of the target on the display screen until initial movement of the subject in the direction of the target.

14. The method of claim 13 wherein the enabling detections are analyzed to determine performance capabilities of said subject or to detect presence of performance abnormalities of said subject.

15. The method of claim 13, further comprising calculating an accumulated time that the subject remained in compliance with the spontaneous visual cues on the display.

16. The method of claim 13, wherein the virtual environment includes an analog and digital speedometer.

17. The method of claim 13, further comprises providing visual cues that prompt the subject to move progressively faster in predictable fashion while simultaneously moving in a movement vector reflective of various targets in the virtual environment.

* * * * *